(12) United States Patent
Fuglerud et al.

(10) Patent No.: US 7,341,706 B2
(45) Date of Patent: Mar. 11, 2008

(54) METHOD OF SYNTHESISING CRYSTALLINE MICROPOROUS METALLOALUMINOPHOSPHATE FOR A SOLID BODY

(75) Inventors: Terje Fuglerud, Porsgrunn (NO); Arne Gidløv Grønvold, Porsgrunn (NO); Eddy Walther Hansen, Oslo (NO); Ivar Martin Dahl, Oslo (NO); Åse Slagtern, Oslo (NO); Rune Wendelbo, Oslo (NO)

(73) Assignee: Polymers Holding AS, Oslo (NO)

( * ) Notice: Subject to any disclaimer, the term of this patent is extended or adjusted under 35 U.S.C. 154(b) by 388 days.

(21) Appl. No.: 10/494,862

(22) PCT Filed: Nov. 6, 2002

(86) PCT No.: PCT/NO02/00407

§ 371 (c)(1),
(2), (4) Date: Jul. 20, 2004

(87) PCT Pub. No.: WO03/040037

PCT Pub. Date: May 15, 2003

(65) Prior Publication Data

US 2005/0003956 A1    Jan. 6, 2005

(30) Foreign Application Priority Data

Nov. 7, 2001    (NO) .................................. 20015437

(51) Int. Cl.
*C01B 37/06*  (2006.01)
*C01B 37/08*  (2006.01)
*C01B 39/04*  (2006.01)
*C01B 39/54*  (2006.01)
*B01J 29/84*  (2006.01)
*B01J 29/85*  (2006.01)
*C07C 1/20*   (2006.01)

(52) U.S. Cl. ...................... 423/702; 423/705; 423/706; 423/707; 423/712; 423/716; 423/305; 423/306; 502/60; 502/62; 502/208; 502/214; 585/638; 585/640

(58) Field of Classification Search ................ 423/712, 423/716, 305, 306, 702, 705, 706, 707; 502/208, 502/214, 60, 62; 585/638, 640
See application file for complete search history.

(56) References Cited

U.S. PATENT DOCUMENTS

| 4,861,743 | A |   | 8/1989  | Flank et al. |
| 4,973,785 | A |   | 11/1990 | Lok et al. |
| 5,514,362 | A |   | 5/1996  | Miller |
| 6,004,527 | A | * | 12/1999 | Murrell et al. ............... 423/712 |

* cited by examiner

*Primary Examiner*—David M Brunsman
(74) *Attorney, Agent, or Firm*—Wenderoth, Lind & Ponack, L.L.P.

(57) ABSTRACT

The invention concerns a simple and cheap method for production of microporous crystalline metalloaluminium-phosphates (ELAPO) for use as adsorbent or catalyst by wholly or partially filling the pores of particles containing aluminum phosphate (AIPO) with an aqueous mixture containing an active source of metal and an organic structure directing agent and perform crystallization at elevated temperature under autogenous pressure to form crystals of ELAPO.

50 Claims, 16 Drawing Sheets

METHOD OF SYNTHESISING CRYSTALLINE MICROPOROUS METALLOALUMINOPHOSPHATE FOR A SOLID BODY

This application is a 371 filing of PCT/NO02/00407, filed 06 Nov. 2002.

The present invention concerns a method of synthesising metallo aluminophosphates (ELAPO), and more particularly to synthesise crystalline microporous silico aluminophosphates (SAPO) of the molecular sieve type, from a solid body and also use of this product as a catalyst for methanol to olefin (MTO) production.

ELAPOs are molecular sieves which have a three-dimensional microporous framework structure of $AlO_2$, $PO_2$ and $ELO_2$ tetrahedral units. Generally the ELAPOs have a chemical composition on an anhydrous basis expressed by the empirical formula of:

$$(H_w El_x Al_y P_z)O_2$$

where EL is a metal selected from the group consisting of silicon, magnesium, zinc, iron, cobalt, nickel, manganese, chromium and mixtures thereof, "x" is the mole fraction of EL and has a value of at least 0.005, "y" is the mole fraction of Al and has a value of at least 0.01, "z" is the mole fraction of P and has a value of at least 0.01, w is the mole fraction of H and x+y+z=1.

The silico aluminium phosphates constitute a generic class of non-zeolite molecular sieve materials being capable of undergoing complete and reversible dehydration while retaining the same essential framework topology in both the anhydrous and hydrated state.

The silico aluminium phosphates, SAPO-34 and SAPO-18, are the catalysts of choice for the MTO-reaction. SAPO-34 has chabasite (CHA) structure and is usually synthesised from an alumina source, a silica source, a phosporous source and at least one structure directing agent. This structure directing agent is usually tetraethyl ammonium hydroxide (TEAOH). A water dispersion of the gel resulting from mixing the components above, is hydrothermally treated at a temperature from 150-260° C. under autogenous pressure to crystallise the SAPO-34. The structure directing agent is usually removed by heating in an oxygen-containing atmosphere (500-700° C.). The calcined material contains acidic protons and has catalytic properties.

In a traditional wet synthesis of SAPO-34 (as in U.S. Pat. No. 4,440,871), the material crystallises with Si/Al ratio of 0.17, corresponding to what can be called high-Si SAPO-34. By altering the synthesis conditions (Si/Al ratio lower than 0.17) it is possible to produce a SAPO-34 with lower Si contents (U.S. Pat. No. 5,191,141 and U.S. Pat. No. 5,912,393). By using Si/Al ratios lower than 0.17 one can also obtain structures with AEI structure (SAPO-18; U.S. Pat. No. 5,609,843), intergrowths of SAPO-34 and SAPO-18 (U.S. Pat. No. 6,334,994) or AFI-structure (SAPO-5). In a typical wet synthesis of SAPO-18, the structure crystallises with a Si/Al ratio of 0.06. XRD analysis will reveal information on the presence of SAPO-34 or SAPO-18. These structures are defined in Atlas of Zeolites Structure Types, W. M. Meier and D. H. Olson, Second Revised Edition 1987, by Butterworths.

U.S. Pat. No. 4,861,743 teaches a process for the production of a crystalline non-zeolitic molecular sieve in a preformed body or carrier. Contacting a liquid reaction mixture with spray-dried particles or extrudates of alumina or silica-alumina at hydrothermal conditions produces the crystalline non-zeolitic molecular sieve. The liquid reaction mixture contains a reactive source of phosphorous pentoxide and an organic structure directing agent. The crystallisation takes place at elevated pressure and temperature and the preformed body reacts with the liquid mixture to form non-zeolitic molecular sieves within the body. Phosphorous can be an active component in the liquid or on the solid alumina or silica-alumina. Likewise, if the non-zeolitic molecular sieve contains silica, the reactive source of silica can be included in the body and/or in the liquid reaction mixture. If the non-zeolitic molecular sieve is to contain one or more elements other than aluminium, silicon and phosphorus, the reactive sources of these elements may be included in the silica or silica-alumina body and/or in the liquid reaction mixture. The smallest amount of water used in this procedure is 25 moles of water per mole of aluminium. Thus, only alumina or silica-alumina is used as the preformed body. All other reactive components are either impregnated on the body or in the liquid mixture. The preparation method that is described is liquid synthesis with excess liquid that needs to be removed afterwards.

In U.S. Pat. No. 5,514,362 synthesis of SAPO-5, SAPO-11, SAPO-31 and SAPO-39 from dense mixtures of alumina and silica gel is described, with no excess liquid to be removed. The dense gel can be formed into self-supporting particles and the shape of the particles is preserved after crystallisation. The gel comprises alumina, silica, structure directing agent and an active source of phosphorous. In all examples the dense gel is extruded into particles before the crystallisation process takes place. The molecular sieve crystallites formed are smaller than those generally formed in conventional processes.

European Patent Application No. 1002764 describes a method for the preparation of small zeolite crystals inside a porous support material with pores smaller than 1000 Å. In this way the size of the zeolite crystals can be controlled. The porous support material is preferably removable in order to isolate the pure zeolite or it is useful as component of a desired catalyst. Typical support materials are carbon or magnesium oxide representing the group of removable porous support materials and silica alumina, which may be a desirable constituent of the catalyst. To obtain the product the support material is impregnated with a synthesis gel consisting essentially of a zeolite precursor composition comprising hydrated oxides of Si, Al and P, metal compounds and a zeolite structure directing agent. The advantages of the method are to prepare small crystallites and the porous support material is used to control the crystallite size. The porous support material is not an active source of the crystallised zeolite.

U.S. Pat. No. 6,004,527 relates to a "dry" process for the production of a large pore molecular sieve by impregnating a solid cation oxide-framework-structure with other reagents suitable for hydrothermal reaction between these reagents and the solid cation oxide-framework-structure to form an impregnated paste-free composition. Then the impregnated paste-free composition is subjected to conditions of temperature and pressure to effect a hydrothermal reaction and convert the reagents of the reaction into a crystalline molecular sieve that possesses the morphologic characteristics of the solid cation oxide-framework-structure. Production of zeolite particles from silica is exemplified.

One object of the present invention is to obtain a cheap, simple and environmentally friendly production method for catalysts and adsorbants of the metallo alumino phosphate type (ELAPO). Production of silicoaluminophosphate (SAPO) is of special interest.

Another object is to synthesise SAPO crystallites with suitable size and composition for methanol to olefin production. It is of special interest to produce materials containing SAPO-34, SAPO-17 and/or SAPO-18, these materials being suitable for the methanol to olefins (MTO) reaction. A third object is, through the synthesis of SAPO-5, SAPO-11 and SAPO-20 to show the general applicability of the described synthesis method.

BRIEF DESCRIPTION OF THE DRAWINGS

These and other objects of the invention are obtained with the method as described below. The invention is further defined and characterised by the enclosed patent claims. The invention will be further documented with reference to the FIGS. 1-14, where:

Figure 1:
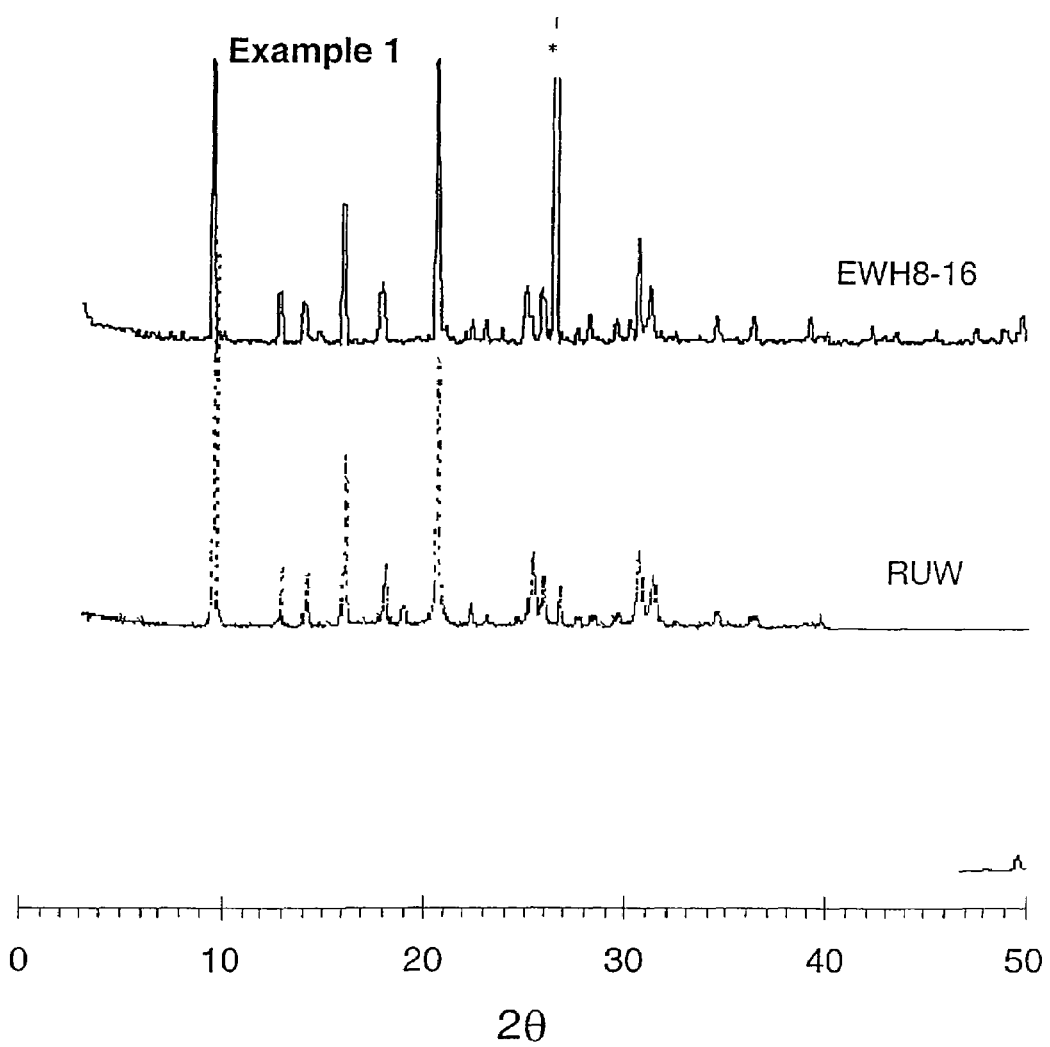
FIG. 1 shows the XRD pattern of the product from Example 1.

The invention thus concerns a method of synthesising crystalline microporous metallo alumino phosphate (ELAPO) from a solid body, where the body consists of particles containing Al and P. The pores of the particles are wholly or partly filled with a liquid reaction mixture, comprising an active source of the EL metal, an organic structure directing agent and water. The crystallisation is performed at elevated temperature under autogenous pressure to form crystals of microporous ELAPO, where the EL metal is selected from the group consisting of silicon, magnesium, zinc, iron, cobolt, nickel, manganese, chromium and mixtures thereof. The EL metal could also be part of the solid body and in this case the liquid reaction mixture could be used with or without an active source of the EL metal. It is preferred to use silicon as the EL metal and produce crystalline microporous SAPO. AlPO particles could be contained in the body and they could also have an outer silica shell. It is preferred to use AlPO where P/Al=1.2-0.6 and to carry out the synthesis in the absence of an external liquid. The particles could be calcined prior to the treatment. The hydrothermal reaction time is 2-120 hours, preferably 4-20 hours. The crystallisation should be performed at temperatures from 150-260° C., preferably 200-220° C. The structure directing agent may be selected from tetraethyl ammonium hydroxide (TEAOH), isopropylamine (IPA), di-isopropylamine (DPA), tripropylamine (TPA), cyclohexylamine (CHA), tri-ethylamine (TEA) or tetramethyl-ammonium-hydroxide (TMAOH). The ratio between the liquid volume and pore volume (measured by liquid volumetric $N_2$ adsorption) is 0.1-7, preferably 1-4 and most preferably 1-3. Surprisingly it was also found that it was possible to produce SAPO from a reaction mixture without stirring of the reactants. It is preferred to produce SAPO-34, SAPO-17 and/or SAPO-18. SAPO-5, SAPO-11 and SAPO-20 could also be produced. The product could be used as adsorbant or as catalyst for the conversion of methanol to light olefins. The particles produced could also be used as catalysts for the production of olefins from an oxygenate containing feedstock comprising at least one compound selected from the group consisting of methanol, ethanol, n-propanol, iso-propanol, C4-C20 alcohols, methyl ethyl ether, dimethyl ether, diethyl ether, di-isopropyl ether, formaldehyde, dimethyl carbonate, dimethyl ketone, acetic acid and mixtures thereof.

With the expression "pores" is meant all pores in the product, while "pore volume" is the volume as measured by liquid volumetric $N_2$ adsorption.

In contrast to earlier known preparation methods, aluminium phosphate could be used as the active source for both aluminium and phosphorous when preparing ELAPOs. The aluminium phosphate is used in the form of porous particles. The AlPO particles might be precipitated by various methods, depending on the desired properties.

For preparation of SAPOs, silica sol or fumed silica are preferred active sources of silicon. Silica gel and silica hydrogel, silicates, silicic acid, colloidal silica, silica hydroxides, alkoxides of silicon, and reactive solid amorphous precipitated silica are also suitable. The silica may be prereacted with the solution of the structure directing agent, or silica may be present as a physical mixture with the porous aluminiumphospate, or as a silico aluminium phosphate.

An organic structure directing agent is added to facilitate crystallisation of the molecular sieve. A mixture of two or more different structure directing agents could also be used. Suitable structure directing agents include tetraethyl ammonium hydroxide (TEAOH), isopropylamine (IPA), di-isopropylamine (DPA), tripropylamine (TPA), cyclohexylamine (CHA), tri-ethylamine (FEA) and tetramethyl-ammonium-hydroxide (TMAOH).

For the preparation of SAPOs, porous AlPO particles are mixed with a small amount of water, a silicon source and a solution containing a structure directing agent to saturate the pores of the particles. The water content is so small that the mixture appears dry, thus the term "dry synthesis" is used. Another term for this technique is incipient wetness. Alternatively the Si source can be present as a separate phase of the solid AlPO or as a silico aluminium phosphate mixture. Slightly different mixing procedures may be used in preparing the reaction mixtures, for instance, by changing the order of which the fluids and AlPO are added. Preferably, the mixing of reactants is performed by an incipient wetness technique and will result in a liquid volume-to-pore volume ratio between approximately 0.1-7, preferably 1-4, and most preferably 1-3. The reaction mixture is placed in a sealed pressure vessel, preferably lined with an inert plastic material such as polytetrafluorethylene. The reaction mixture is heated under autogenous pressure at a temperature in the range of 150° C. to 260° C., preferably at a temperature of 200-220° C. for a period of from a few hours to some days, typically 2-120 hours, preferably about 4-20 hours. The crystallisation occurs in absence of a continuous liquid phase. The idea is that one or more SAPOs (e.g. SAPO-34/SAPO-18/SAPO-5) are nucleated inside the pores of the carrier particle. The as synthesised product is calcined at 500-600° C. for a few hours in dry air in order to remove the organic structure directing agent from the pores of the crystalline material. The resulting molecular sieve comprises a three-dimensional microporous crystal framework comprising a SAPO microporous structure.

After SAPO synthesis, particles may be prepared from a mixture of the crystallised material and a suitable binder (e.g. fluidised bed particles).

Materials suitable for use in fluidised bed reactors are typically produced by spray-drying a slurry of the active catalyst. Additional materials are generally added to the slurry in order to adjust the physical properties and the mechanical strength of the final particle.

When preparing SAPO-34 by "dry-synthesis" from a porous AlPO mixed with a silica source and structure directing agent /water solution the following substitution will take place:

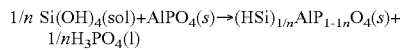

where n>1.

This corresponds to using 1 mol base/Si and up to 3 moles of base to neutralise the phosphoric acid. Since it is probably not necessary with a complete neutralisation (3 moles of base) of the phosphoric acid, only 1-2 moles of base may be adequate for this neutralisation.

This suggests that an AlPO having P/Al of approximately 0.8 (1.2-0.6) is more suitable for synthesis of SAPO-34 with Si/Al ratio 0.17. For synthesis of SAPO-34/SAPO-18 with Si/Al ratio around 0.06 it is more suitable with an AlPO with P/Al of 0.9-1. One advantage of using an AlPO with P/Al ratio adjusted to the amount of Si used in the synthesis, is to minimise the amount of structure directing agent needed for the synthesis, or for making extra base addition unnecessary.

It would also (when using AlPO with P/Al=1) be unnecessary to use the more costly template, TEAOH, as a neutralising agent. For instance, isopropyl amine (IPA) may be used. Hence, to make the synthesis more cost-effective a significant amount of the structure directing agent TEAOH may be replaced by IPA.

The present synthesis method has the following advantages compared to prior art:

A. The use of a porous AlPO as precursor for the microporous crystalline silico-aluminophosphate makes it possible to use considerably smaller amounts of structure directing agent, as well as making it possible to use cheaper amines as part of a structure directing agent mixture.

B. The use of less water (compared to $H_2O/Al=25$ in U.S. Pat. No. 4,861,743 and $H_2O/Al=17.5$-$22.5$ in U.S. Pat. No. 6,207,872 and $H_2O/Al=15$ in Lok et al U.S. Pat. No. 4,440,871 (Example 25), $H_2O/Al$ are mainly 5-10 in this invention) during the hydrothermal synthesis compared to prior art, makes it unnecessary to filtrate and wash the product and avoids cleanup of contaminated water.

C. The intimate mixing of liquid and solid established in filling the pores of the solid with the synthesis liquid makes stirring of the synthesis mixture unnecessary, simpler autoclaves could thus be used for the hydrothermal synthesis stage.

D. The intimate contact between solid and liquid also gives a higher nucleation rate and a higher crystallisation rate, resulting in less reaction times needed, and giving crystallites of size 0.2-1 μm, compared to 0.5-3 μm for a SAPO-34 synthesised after the method of Lok et.al in U.S. Pat. No. 4,440,871. The smaller particle size gives a MTO catalyst with higher durability and expected higher rate of absorption.

E. By using this method it is possible to vary the Si/Al ratio to a wide extent and obtaining SAPO-34 as well as SAPO-18. By using Si/Al ratios in the range of 0.03-0.06, materials containing SAPO-34, SAPO-18 and mixtures thereof in various proportions can be made. Under certain process conditions, these may have improved deactivation properties as well as higher olefin selectivities in the MTO process.

EXAMPLES

The invention will be further illustrated by the examples to follow.

A description with characteristics of the different AlPO materials used in the present invention is given in Table 1. The porosity of the materials was characterised by liquid $N_2$ adsorption and elemental composition by XRF.

TABLE 1

Characteristics of the different AlPOs used in the present invention. Unless otherwise stated in the text, all samples were calcined at 400° C. for 16 hours before use.

| Name | Preparation | P/Al | $N_2$-BET ($m^2$/g) | $N_2$-volume (cc/g) | Pore diameter (Å) |
|---|---|---|---|---|---|
| AlPO-light | Commercial, Riedel-de-Hahn; EG-no.: 232-056-9; Lot 914110 calcined 600° C. | 1.1 | 14 | | |
| K00-053.001 | Powder from Grace, Worms, Germany, LOT SP2 7980-01 | 1.0[1] | 100 | 0.66 | 220 |
| K00-058.001 | Powder produced[2], aceton washed, vacuum dried, calcined | 0.8 | 230 | 0.41 | 60 |
| K00-077.001 | Powder from Grace, Worms, Germany, LOT SP2 7980-02 | 1.0[1] | 106 | 0.71 | 220 |
| K00-077.008 | K00-077.001 spray dried | 0.9 | 140 | 0.64 | 180 |
| K00-102.003 | Powder produced[2], spray dried | 0.95 | 177 | 0.47 | 90 |
| K00-092.004 | Powder produced[2], spray dried | 1.0 | 160 | 0.44 | 100 |
| K00-218.002 | Powder produced[2] | 1.0 | 192 | 0.60 | 100 |

[1]specification from supplier
[2]synthesised according to the method given in U.S. Pat. No. 4364855

Preparation of the Aluminium Phosphates Used

The aluminium phosphate powders produced and given in Table 1 were synthesised according to the method given in U.S. Pat. No. 4,364,855. The resulting gels were washed and filtrated repeatedly to remove $NH_4NO_3$, followed by drying at 100° C. and calcination in an oven at 400° C. for 16 h. The spray dried samples were produced from a water slurry in a conventional spray drier. The material denoted K00-092.004 was spray dried from a slurry with added Ludox LS30 so as to have 20 weight % $SiO_2$ in the final particle.

If not otherwise stated in the text, a stainless steel autoclave with a Teflon liner of volume 40 ml was used and a synthesis temperature of 210° C. A detailed overview of all synthesis presented in this invention are listed in Table 2.

If not otherwise stated, the following reagents are used:
Silica source: Ludox LS30; 30 weight % suspension in water (pH=8.2), Du Pont product
TEAOH (tetraethyl ammonium hydroxide; Aldrich; 35 weight %)
IPA (isopropylamine; Fluka; 99.5 weight %)
DPA (di-isopropylamine; Fluka; 99 Weight %)
TEA (Tri-ethylamine, Janssen 99% 15.791.77)
TPA (Tripropylamine, Fluka, 98 weight %)
TMAOH (Tetramethyl ammonium hydroxide-pentahydrate; Fluka, 9 weight %)

The AlPO materials used in this invention are detailed in Table 1.

XRD Analysis

The products were analysed using an X-ray powder diffractometer, Siemens D-5000, which produces monochromatic radiation (from a $CuK_{\alpha1}$ source) of wavelength equal to 1.54056 Å. Most of the XRD patterns presented in this invention are displayed along with the XRD pattern of a reference SAPO-34 obtained by a conventional wet synthesis procedure essentially like that in U.S. Pat. No. 4,440,871 (B. M. Lok et al., Example 35). The diffraction pattern of this latter reference sample is denoted "RUW" in the Figures.

TABLE 2

A detailed overview of all synthesis presented in the present invention

| Ex no. | AlPO | Sample | Mass weights (g) | | | | | Mol-weight (mmol) | | | | | | Time[1] (hours) |
| | | | AlPO | Ludox | TEAOH | IPA | Water | AlPO | SiO2 | TEAOH | IPA | Water | V/V$_p$ | |
|---|---|---|---|---|---|---|---|---|---|---|---|---|---|---|
| 1 | AlPO-light | EWH8-16 | 8.0 | 2.0 | 14.0 | 0 | 5.0 | 66 | 10 | 33 | 0 | 861 | | 72 |
| 2 | AlPO-light | EWH8-10 | 5.0 | 3.1 | 8.8 | 0 | 3.1 | 41 | 16 | 21 | 0 | 362[2] | | 42 |
| 3 | AlPO-light | EWH8-11 | 5.0 | 3.1 | 8.8 | 0 | 3.1 | 41 | 16 | 21 | 0 | 125[3] | | 42 |
| 4 | K00-053.001 | EWH11-6 | 2.0 | 0.26 | 1.86 | 0 | 0 | 16.4 | 1.3 | 4.4 | 0 | 77.3 | ~2.5 | 20 |
| 5 | K00-058.001 | EWH12-4 | 2.0 | 0.85 | 1.78 | 0 | 0 | 16.4 | 4.2 | 4.2 | 0 | 97 | ~2.0 | 20 |
| 6 | K00-077.008 | EWH15-8 | 2.0 | 1.18 | 2.48 | 0 | 0 | 16.4 | 5.9 | 5.9 | 0 | 135 | ~2.5 | 20 |
| 7 | K00-102.003 | EWH16-7 | 2.0 | 1.52 | 3.2 | 0 | 0 | 16.4 | 7.6 | 7.6 | 0 | 175 | ~4.7 | 20 |
| 8 | K00-092.004 | EWH17-8 | 2.0 | 0.12 | 2.6 | 0 | 0 | 16.4 | 0.62/7[4] | 6.2 | 0 | 99 | ~3.0 | 20 |
| 9 | K00-092.004 | EWH17-4 | 2.0 | 0 | 2.7 | 0 | 0 | 16.4 | 0/7[4] | 6.4 | 0 | 98 | ~3.0 | 20 |
| 10 | K00-218.002 | ABA135-1 | 2.0 | 0.55 | 2.3 | 0 | 0 | 16.4 | 2.7 | 5.5 | 0 | 104 | | 20 |
| 11 | K00-218.002 | ABA135-2 | 2.0 | 0.55 | 2.3 | 0.16 | 0 | 16.4 | 2.7 | 5.5 | 2.7 | 104 | | 20 |
| 12 | K00-218.002 | ABA135-3 | 2.0 | 0.55 | 2.3 | 0.32 | 0 | 16.4 | 2.7 | 5.5 | 5.4 | 104 | | 20 |
| 13 | K00-218.002 | ABA135-4 | 2.0 | 0.55 | 2.3 | 0.48 | 0 | 16.4 | 2.7 | 5.5 | 8.1 | 104 | | 20 |
| 14 | K00-218.002 | ABA135-5 | 2.0 | 0.55 | 2.3 | 0.64 | 0 | 16.4 | 2.7 | 5.5 | 10.8 | 104 | | 20 |
| 15 | K00-218.002 | ABA136-1 | 2.0 | 0.55 | 0 | 0.32 | 1.82 | 16.4 | 2.7 | 0 | 5.4 | 122 | | 20 |
| 16 | K00-218.002 | ABA136-2 | 2.0 | 0.55 | 1.15 | 0.32 | 0.68 | 16.4 | 2.7 | 2.7 | 5.4 | 100 | | 20 |
| 17 | K00-218.002 | ABA136-3 | 2.0 | 0.55 | 2.3 | 0.32 | 0 | 16.4 | 2.7 | 5.5 | 5.4 | 104 | | 20 |
| 18 | K00-218.002 | ABA136-4 | 2.0 | 0.55 | 3.45 | 0.32 | 0 | 16.4 | 2.7 | 8.2 | 5.4 | 145 | | 20 |
| 19 | K00-218.002 | ABA136-5 | 2.0 | 0.55 | 4.60 | 0.32 | 0 | 16.4 | 2.7 | 10.9 | 5.4 | 187 | | 20 |
| 20 | K00-092.004 | EWH18-1 | 2.0 | 0 | 6.1 | 0 | 0 | 16.4 | 0/7[4] | 14.5 | 0 | 220 | ~6.8 | 20 |
| 21 | K00-092.004 | EWH18-2 | 2.0 | 0 | 3.8 | 0.34 | 1.50 | 16.4 | 0/7[4] | 9.0 | 5.8 | 220 | ~6.5 | 20 |
| 22 | K00-092.004 | EWH18-4 | 2.0 | 0 | 0 | 0.85 | 4.0 | 16.4 | 0/7[4] | 0 | 14.4 | 222 | ~5.9 | 20 |
| 23 | K00-218.002 | ABA127 | 60 | 16.4 | 69.1 | 0 | 0 | 492 | 82 | 164 | 0 | 3133 | | 20 |
| 24 | K00-218.002 | ABA139-3 | 2.0 | 0.55 | 2.3 | 0 | 0 | 16.4 | 2.7 | 5.5 | 0 | 104 | | 20 |
| 25 | K00-218.002 | ABA139-4 | 2.0 | 0.55 | 2.3 | 0 | 0 | 16.4 | 2.7 | 5.5 | 0 | 104 | | 20 |
| 26 | K00-218.002 | ABA140-1 | 2.0 | 0.55 | 2.3 | 0 | 0 | 16.4 | 2.7 | 5.5 | 0 | 104 | | 20 |
| 27 | K00-218.002 | ABA140-2 | 2.0 | 0.55 | 2.3 | 0 | 0.5 | 16.4 | 2.7 | 5.5 | 0 | 132 | | 20 |
| 28 | K00-218.002 | ABA140-3 | 2.0 | 0.55 | 2.3 | 0 | 1.0 | 16.4 | 2.7 | 5.5 | 0 | 160 | | 20 |
| 29 | K00-218.002 | ABA140-4 | 2.0 | 0.55 | 2.3 | 0 | 3.0 | 16.4 | 2.7 | 5.5 | 0 | 271 | | 20 |
| 30 | K00-053.001 | ABA143-4 | 2.0 | 0.55 | 0 | 0.78[5] | 3.0 | 16.4 | 3.8 | 0 | 5.4 | 186 | ~5.4 | 20 |
| 31 | K00-053.001 | ABA145-2 | 2.0 | 0.55 | 0 | 0.66[6] | 3.2 | 16.4 | 2.7 | 0 | 3.6 | 218 | ~4.8 | 20 |
| 32 | K00-053-001 | ABA145-4 | 2.0 | 0.55 | 0 | 0.99[6] | 2.6 | 16.4 | 2.7 | 0 | 5.4 | 193 | ~4.3 | 20 |
| 33 | K00-058.001 | ABA144-2 | 2.0 | 0.55 | 0 | 0.37[7] | 3.2 | 16.4 | 2.7 | 0 | 3.7 | 199 | ~3.2 | 20 |
| 34 | K00-218.002 | ABA146-1 | 2.0 | 0.55 | 2.3 | 0 | 0 | 16.4 | 2.7 | 5.5 | 0 | 104 | | 20 |
| 35 | K00-218.002 | ABA146-2 | 2.0 | 0.55 | 2.3 | 0 | 0 | 16.4 | 2.7 | 5.5 | 0 | 104 | | 8 |
| 36 | K00-218.002 | ABA146-3 | 2.0 | 0.55 | 2.3 | 0 | 0 | 16.4 | 2.7 | 5.5 | 0 | 104 | | 4 |
| 37 | K00-058.001 | ABA147-2 | 2.0 | 0.8 | 0.8 | 0 | 1.4 | 16.4 | 3.8 | 1.9 | 0 | 136 | | 20 |
| 38 | K00-058.001 | ABA151-3 | 2.0 | 0.4 | 0.8 | 0 | 1.7 | 16.4 | 1.9 | 1.9 | 0 | 138 | | 20 |
| 41[8] | K00-218.002 | ABA-201-1 | 2.44 | 0.67 | 4.2 | 0 | 0 | 20 | 3.3 | 10 | 0 | 178 | ~3.3 | 77[8] |
| 42[8] | K00-218.002 | ABA-201-2 | 2.44 | 0.22 | 4.2 | 0 | 0 | 20 | 1.1 | 10 | 0 | 160 | ~3.0 | 77[8] |
| 43 | K00-218.002 | ABA-202-2 | 2.44 | 0.22 | 4.2 | 0 | 0 | 20 | 1.1 | 10 | 0 | 160 | ~3.0 | 20 |
| 44[9] | K00-218.002 | ABA-204-2 | 2.44 | 0.22 | 4.2 | 0 | 0 | 20 | 1.1 | 10 | 0 | 160 | ~3.0 | 16 + 48[9] |
| 45 | K00-218.002 | ABA 208-1 | 2.44 | 0.22 | 2.10 | 0 | 2 | 20 | 1.1 | 5 | 0 | 196 | ~3.0 | 20 |
| 46 | K00-218.002 | ABA-207-2 | 2.44 | 0.22 | 2.86 | 0 | 0.8 | 20 | 1.1 | 6.8 | 0 | 156 | ~2.6 | 20 |
| 47 | K00-218.002 | ABA-208-2 | 2.44 | 0.22 | 3.53 | 0 | 0.5 | 20 | 1.1 | 8.4 | 0 | 164 | ~2.9 | 20 |
| 48 | K00-218.002 | ABA-207-1 | 2.44 | 0.22 | 4.2 | 0 | 0 | 20 | 1.1 | 10 | 0 | 160 | ~3.0 | 20 |
| 49 | K00-218.002 | ABA-210-2 | 2.44 | 0.22 | 1.43 | 0.34[10] | 1.9 | 20 | 1.1 | 3.4 | [10] | 166 | ~2.7 | 20 |

TABLE 2-continued

A detailed overview of all synthesis presented in the present invention

| Ex no. | AlPO | Sample | Mass weights (g) | | | | | Mol-weight (mmol) | | | | | $V/V_p$ | Time[1] (hours) |
|---|---|---|---|---|---|---|---|---|---|---|---|---|---|---|
| | | | AlPO | Ludox | TEAOH | IPA | Water | AlPO | SiO2 | TEAOH | IPA | Water | | |
| 50 | K00-218.002 | ABA-208-6 | 2.44 | 0.44 | 2.86 | 0 | 1.0 | 20 | 2.2 | 6.8 | 0 | 176 | ~2.9 | 20 |
| 51 | K00-218.002 | ABA-208-5 | 2.44 | 0.11 | 2.86 | 0 | 1.2 | 20 | 0.6 | 6.8 | 0 | 174 | ~2.8 | 20 |

[1] Hydrothermal reaction time, 210° C. if no otherwise stated
[2] Approximately 80 wt % of the water within the reaction mixture was evaporated prior to hydrothermal treatment,
[3] Approximately 40 wt % of the water within the reaction mixture was evaporated prior to hydrothermal treatment,
[4] x/y where x represents the amount of $SiO_2$ from Ludox and y represents the amount of $SiO_2$ within the outer shell of the AlPO,
[5] Tripropylamine
[6] Tetramethylammoniumhydroxide,
[7] Diisopropylamine,
[8] The relative amounts of structure directing agent and Si as well as crystallisation temperature were taken from: U.S. Pat. No. 5191141, Example 5, 77 h at 175° C.,
[9] The relative amounts of structure directing agent and Si as well as crystallisation temperature were taken from: U.S. Pat. No. 5912393, Example 1, 16 h at 100° C., 48 h at 175° C.,
[10] Tri-ethylamine

Example 1

Synthesis of SAPO-34 from AlPO-particles (EWH8-16)

A synthesis mixture was prepared by first adding 2.0 g Ludox LS30 to 8.0 g of a porous AlPO material (K00-102.003, Table 1) and then adding 14.0 g 35% TEAOH and 5.0 g water under thorough mixing. 0.35 g of HCl was added to the water before mixing. The mixture was reacted in a Teflon lined stainless steel autoclave at 210° C. for 72 h. The XRD pattern of the resulting silicoaluminophosphate product is shown in FIG. 1 (EWH8-16), and confirms the formation of an almost pure SAPO-34. The reflection at about 2Θ=26 degrees is assumed to represent a dense $AlPO_4$ phase.

Example 2

Fractional Removal of Water Prior to Hydrothermal Treatment (EWH8-10)

In this preparation, 5.0 g AlPO-light (Table 1) was used as an AlPO source and mixed with 3.1 g Ludox LS30, 8.8 g TEAOH and 3.1 g water using the mixing procedure outlined in Example 2.

Figure 2:
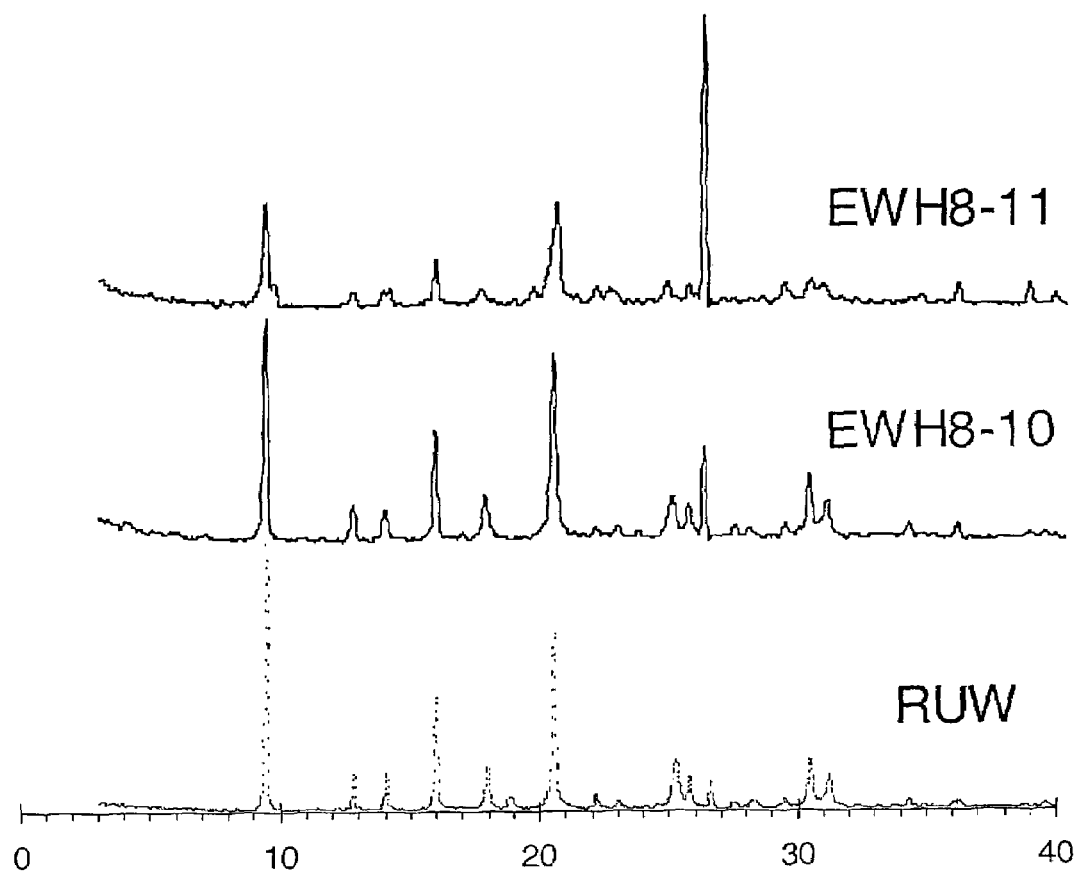
FIG. 2 shows XRD patterns of the products from Examples 2 and 3.

The mixture was heated in an oven at 97° C. until the liquid mass was reduced from 15.0 g to 6.2 g, corresponding to a loss by evaporation of 8.8 g of water, or approximately 80% of the total water content within the original mixture. The mixture was reacted in a Teflon lined stainless steel autoclave at 210° C. for 42 h, and the XRD pattern in FIG. 2 confirms that SAPO-34 was formed.

Example 3

Fractional Removal of Water Prior to Hydrothermal Treatment (EWH8-11)

This preparation is identical to the one in Example 2 except that the amount of water being evaporated was somewhat less, approximately 40 weight % of the total water content within the original sample. The XRD pattern in FIG. 2 confirms that SAPO-34 was formed.

Examples 4-8

Synthesis of SAPO-34 from Different AlPOs (EWH1-6, 12-4, 15-8, 16-7, 17-8)

Five different AlPOs denoted K00-053.001, K00-058.001, K00-077.008, K00-102.003 and K00-092.004 (see Table 1) were tested. In contrast to the preceding synthesis (Examples 1-3), only 2.0 g of AlPO was used in each of the present examples. Also, the "free" volume or the available "gas-volume" of the Teflon-liner was reduced from approximately 40 ml to 3-5 ml by insertion of a compact, cylindrical Teflon insert into the Teflon-liner. The reason for reducing this "free" volume was to limit the amount of water in the vapour phase.

Also, a slightly different mixing procedure was applied as compared to the one described in Examples 2-3, in that Ludox LS30 (0.26 g, 0.85 g, 1.18 g, 1.52 g, 0.12 g respectively), was mixed together with the organic structure directing agent TEAOH (1.86 g, 1.78 g, 2.48 g, 3.2 g, 2.6 g respectively), and the resulting solution added to the AlPO powder by incipient wetness by thorough mixing.

Figure 3:
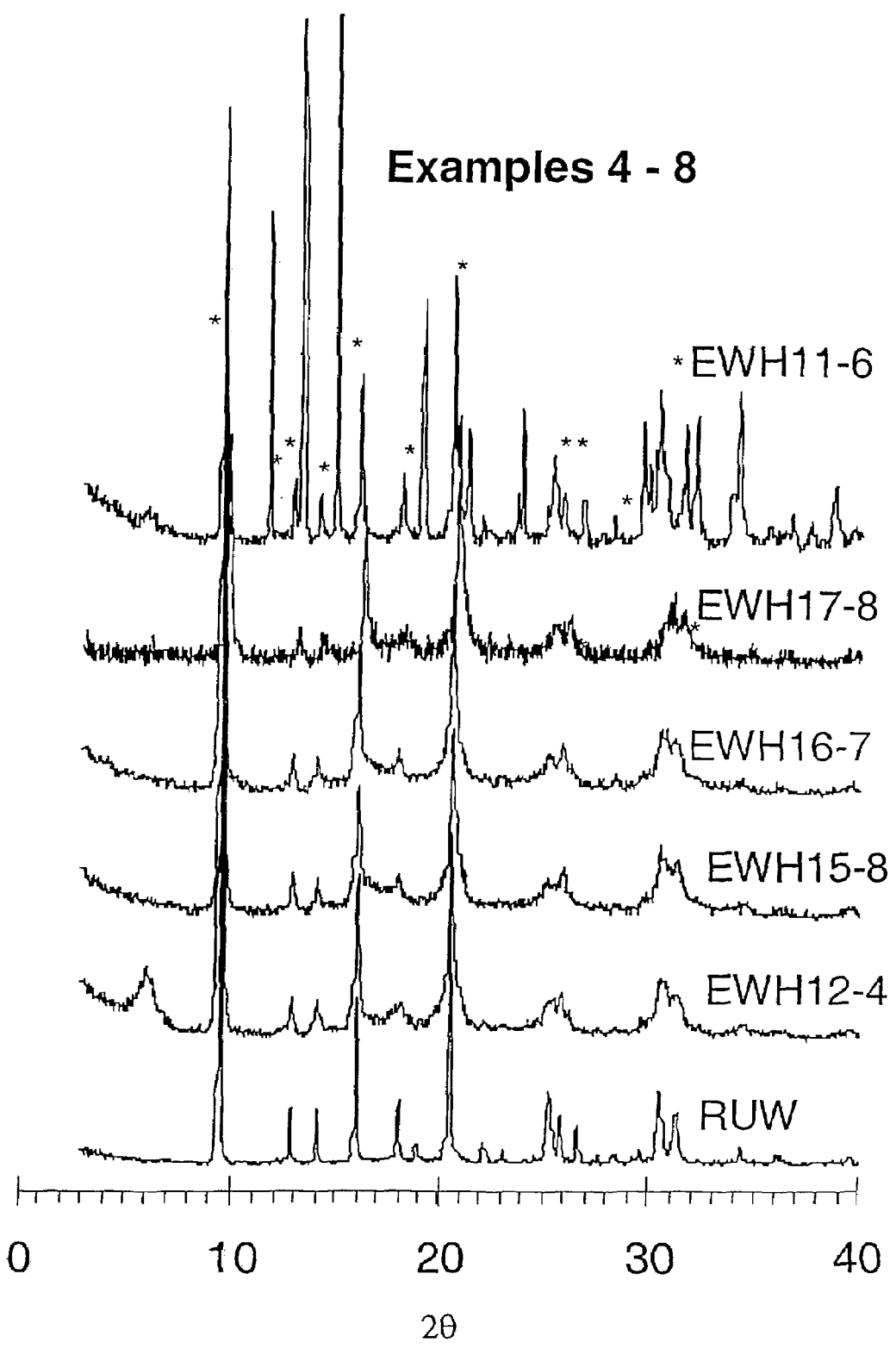
FIG. 3 shows XRD patterns of the products from Examples 4-8.

The mixtures were reacted in Teflon lined stainless steel autoclaves at 210° C. for 20 h. The XRD patterns of the crystalline products (FIG. 3) are all consistent with the formation of SAPO-34. The numerous, additional intense diffraction lines seen in the XRD pattern of sample EWH11-6 originate from aluminium ammoniumhydroxidephosphate.

Example 9

Synthesis of SAPO-34 in the Absence of Ludox (EWH17-4)

Figure 4:
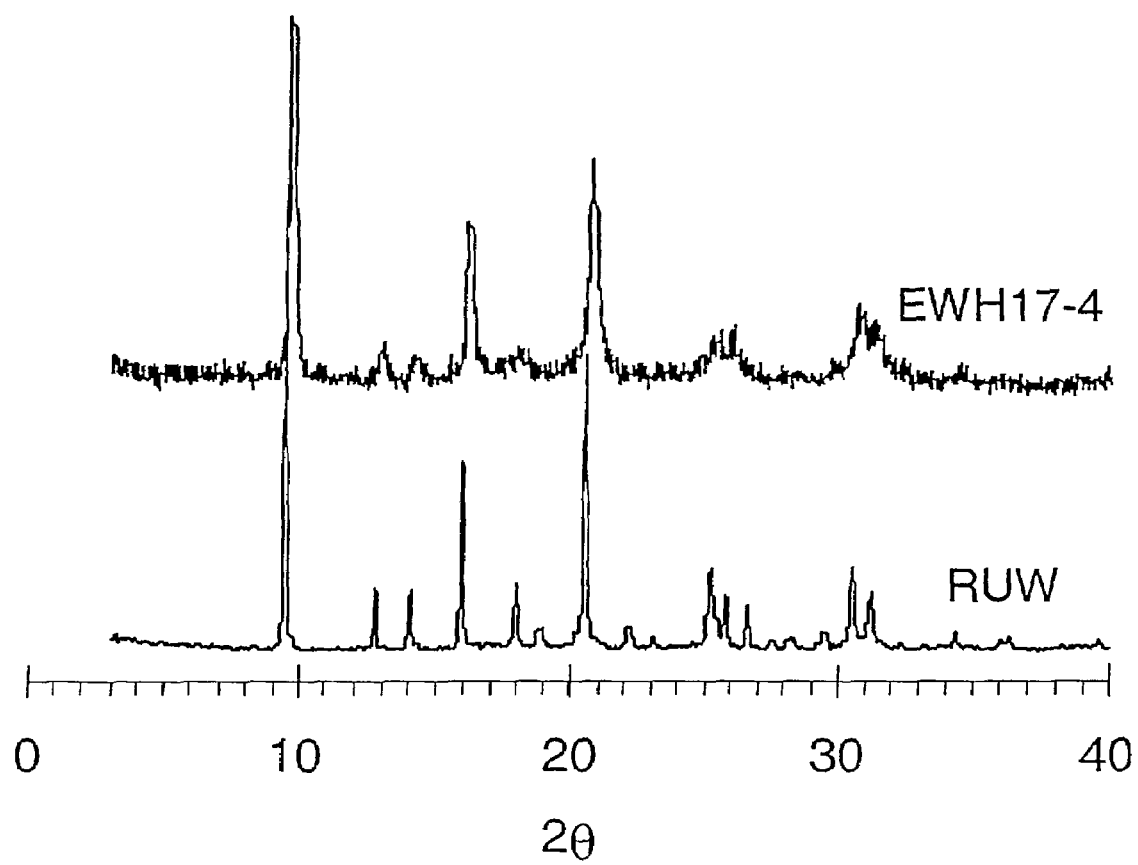
FIG. 4 shows the XRD pattern of the product from Example 9.

The surface of one of the AlPO materials (K00-092.004; Table 1) contained a silica shell, which was formed by spray-drying. The silica content was approximately 20 weight %. 2.7 g TEAOH was added to 2.0 g of the AlPO material by incipient wetness under thorough mixing. The mixture was reacted in a Teflon lined stainless steel autoclave at 210° C. for 20 h. The XRD pattern of the resulting crystalline powders revealed formation of pure SAPO-34 (FIG. 4).

Examples 10-19

Mixture of Two Organic Structure Directing Agents Within One Reaction Mixture (ABA135-1-51136-1-5)

In the following examples, two different synthesis approaches were applied; a) the Si-content and the TEAOH/Si-mole ratio were kept constant and the IPA/Si-mole ratio varied and b) the Si-content and the IPA/Si-mole ratio were kept constant and the TEAOH/Si-mole ratio varied. Table 2 shows the actual amount of reactants used. The AlPO used in these synthesis was K00-218.002 (Table 1). In these Examples Ludox, the organic structure directing agent (s) and AlPO were mixed together and water subsequently added by incipient wetness under thorough mixing.

As in Examples 4-8, the available "free" volume of the Teflon-liner was reduced from approximately 40 ml to only 3-5 ml by inserting a compact, cylindrical Teflon insert into the Teflon-liner. The mixtures were reacted in Teflon lined stainless steel autoclaves at 210° C. for 20 h.

Figure 5A:
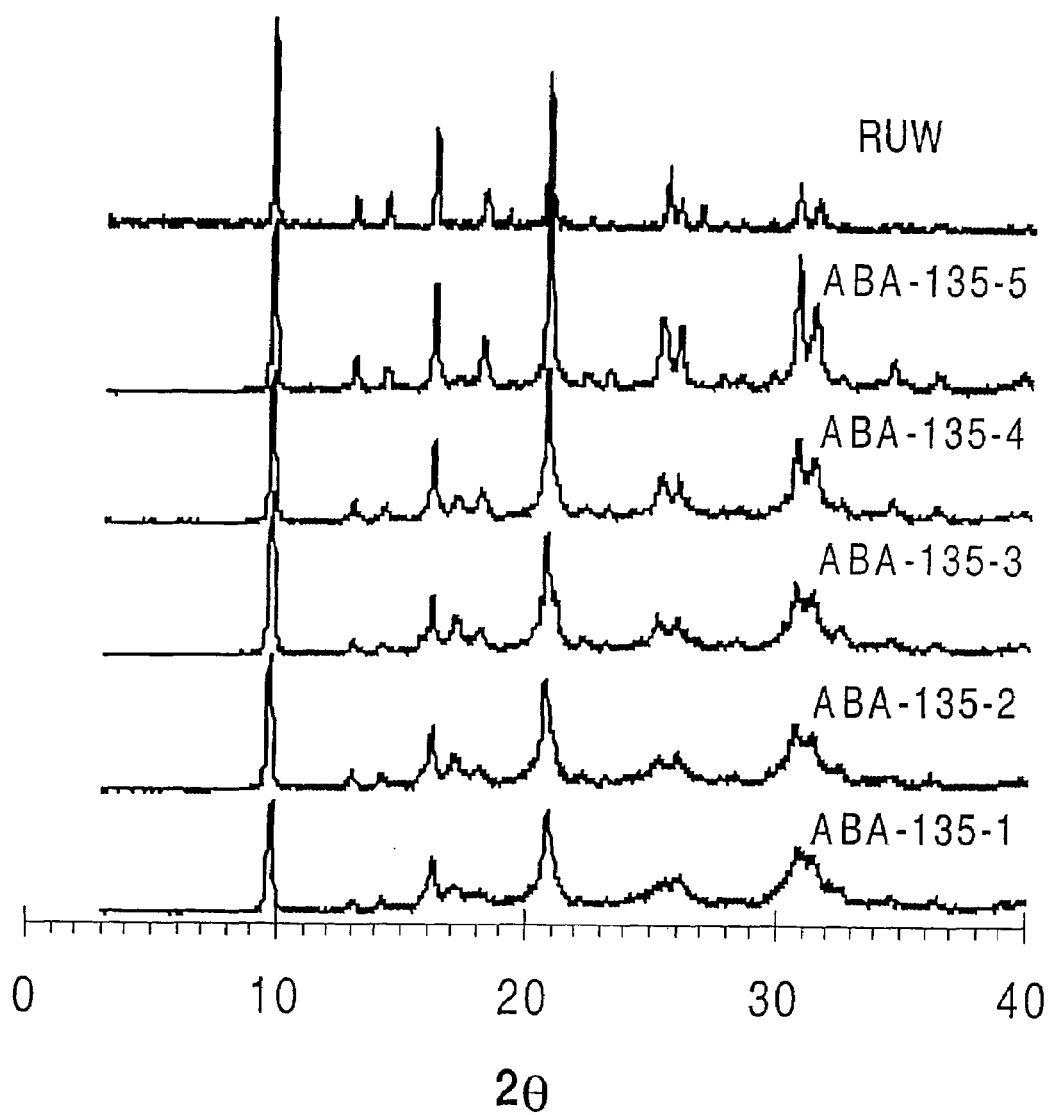
FIG. 5A shows XRD patterns of the products from Examples 10-14.

As indicated by the XRD patterns of the crystalline products (FIGS. 5A and B), SAPO-34 are formed in all preparations, except for ABA-136-1, in which only isopropylamine (IPA) was used as an organic additive.

Two of the synthesised products, ABA-135-5 and ABA-136-2 seem to consist of mostly pure SAPO-34. Both of these samples had—prior to synthesis—the same molar ratio of 2.0 between IPA and TEAOH. Sample ABA-135-5 contained, however, twice as much structure directing agent as compared to sample ABA-136-2.

Figure 5B:
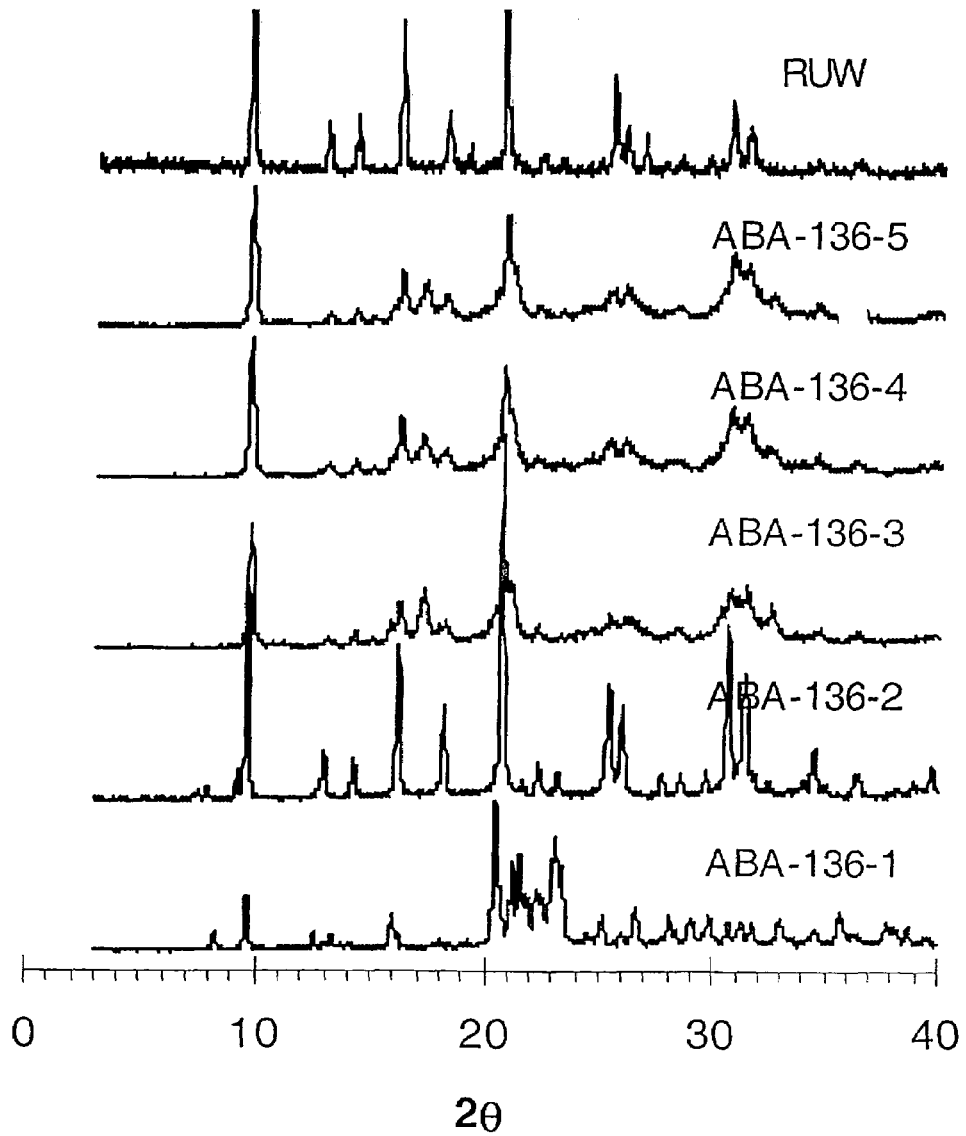
FIG. 5B shows XRD patterns of the products from Examples 15-19.

The XRD patterns of most of the products reveal some minor formation of SAPO-18, as suggested—tentatively—by the appearance of diffraction line $2\theta=17.0$ degrees. As can be concluded from the data in FIG. 5 A, the relative amount of SAPO-34/SAPO-18 depends on the relative concentration of reactants (Table 2) within the synthesis mixture.

Examples 20-22

Mixture of Structure Directing Agents in the Absence of Ludox (EWH18-1, 2 and 4)

Using essentially the same procedure as in Examples 10-19 and replacing the AlPO with K00-092.004 (Table 1) three reaction mixtures were prepared in the absence of Ludox. The composition of the reaction mixtures is summarised in Table 2. The mixtures were reacted in Teflon lined stainless steel autoclaves at 210° C. for 20 h.

Figure 6:
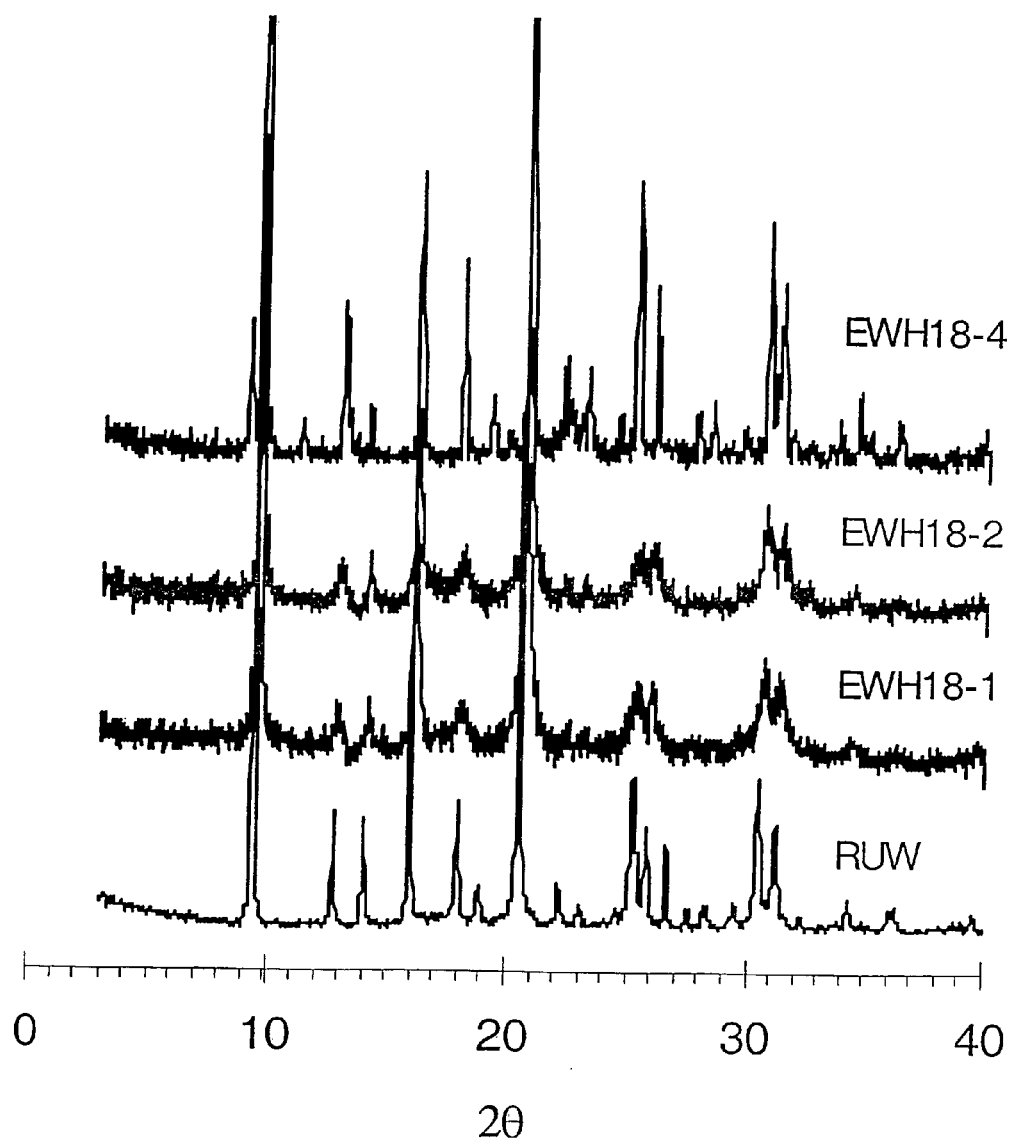
FIG. 6 shows XRD patterns of the products from Examples 20-22.

The XRD pattern of the resulting crystalline powders revealed formation of SAPO-34 (FIG. 6). However, when increasing the relative amount of IPA while keeping the total amount of organic additives (TEAOH and IPA) constant (Table 2), some additional small amount of other crystalline specie(s) were formed.

Example 23

Upscaling (ABA127)

An attempt to upscale the synthesis of SAPO-34 was initiated by increasing the amount of all reactants by a factor of 30 in comparison to Example 10. The smaller Teflon autoclave (40 ml) was replaced by a larger one of approximately 200 ml. Five identical batches were prepared, using 60 g of the AlPO material denoted K00-218.002 in each (Table 1), 16.4 g Ludox LS30 and 69.1 g TEAOH. The reactants were mixed as described in Examples 4-8. The overall liquid volume was approximately twice the available pore volume of the porous AlPO material.

Figure 7A:
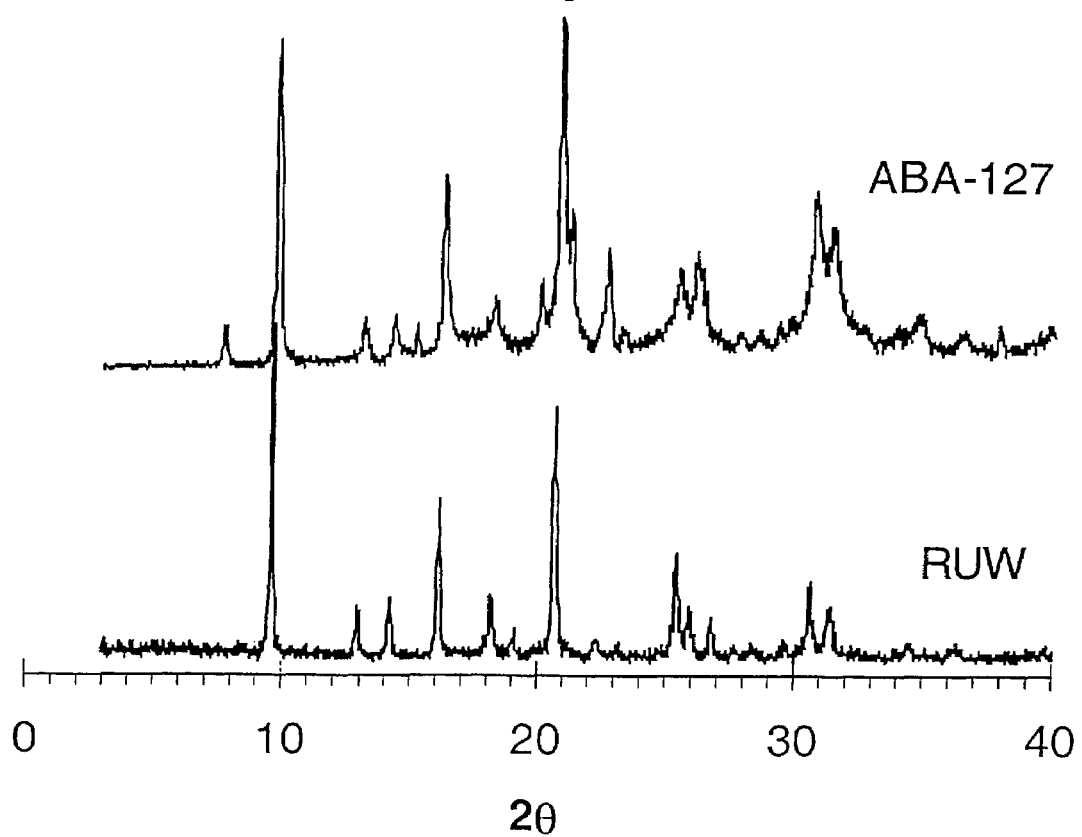
FIG. 7A shows the XRD pattern of the product from Example 23.

The XRD pattern of the resulting crystalline powders revealed essentially SAPO-34 (FIG. 7A). Some small amount of AlPO-18/SAPO-18 seems to form, as tentatively concluded from the observed diffraction line at $2\theta=17.0$ degrees. The XRD of only one of the replicas is shown in FIG. 7A, simply due to the excellent reproducibility observed for the five batches.

Figure 7B:
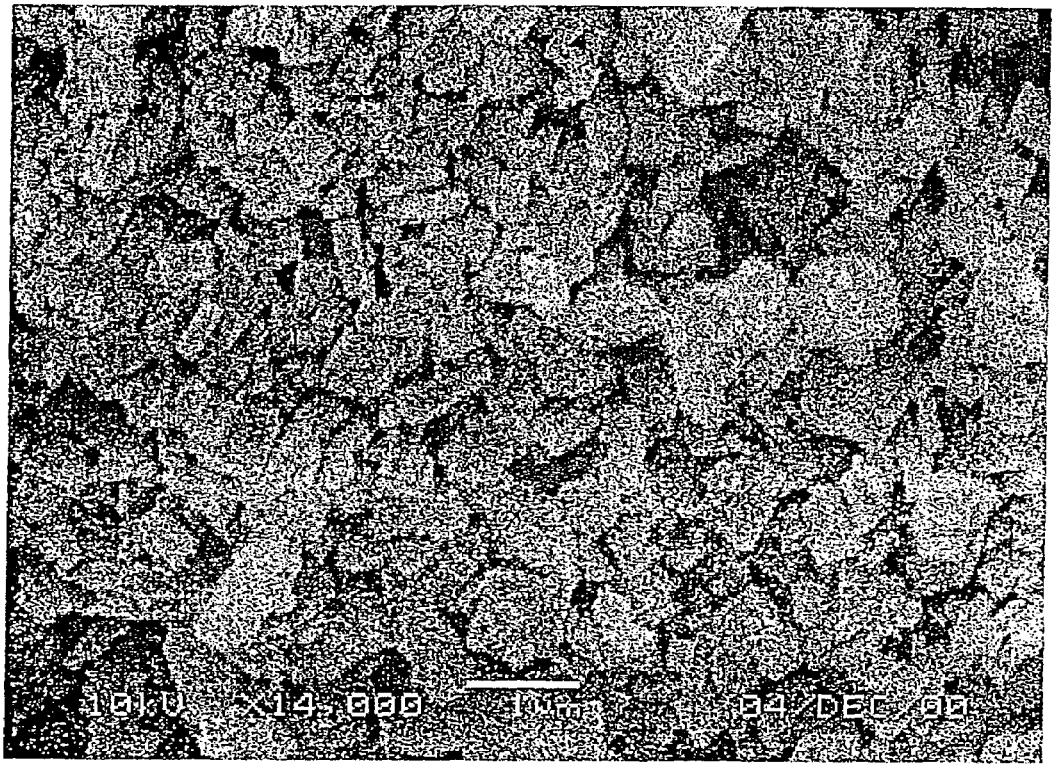
FIG. 7B shows SAPO-34 crystallites.

The size of the regularly shaped SAPO crystallites are typically in the range 0.25 to 1 μm as seen in FIG. 7B.

Examples 24-25

Non-Stirring of Reactants Prior to Hydrothermal Treatment. (ABA139-3 and 4)

2.0 g of an AlPO material K00-218.002 (see Table 1) was mixed with 0.55 g Ludox LS30 together with 2.3 g of an organic additive (TEAOH). Water was subsequently added by incipient wetness under thorough mixing (ABA139-3). To a second and identical AlPO material was added the same type and amount of fluid reactants, without any stirring (ABA139-4). See Table 2 for further details. Both mixtures were reacted in Teflon lined stainless steel autoclaves at 210° C. for 20 h.

Figure 8:
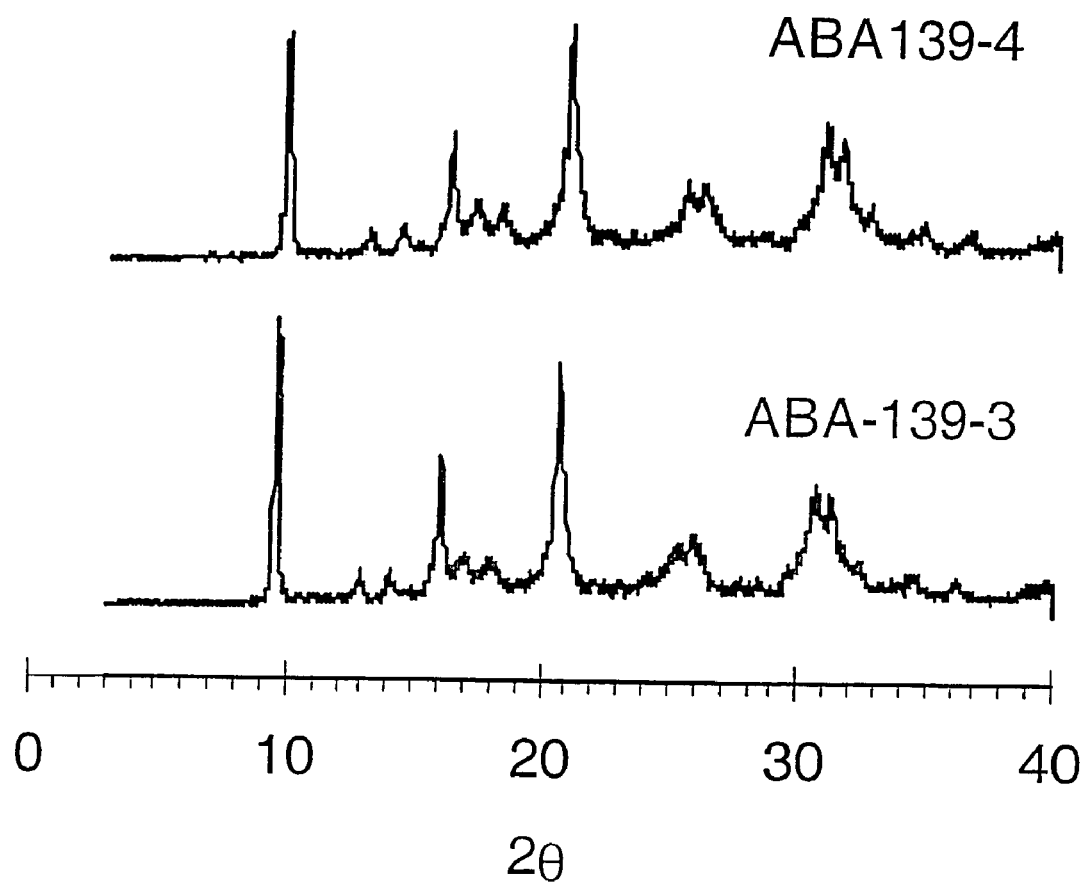
FIG. 8 shows the XRD patterns of the products from Examples 24-25.

As can be confirmed by the XRD patterns (FIG. 8), the two crystalline products were identical. Moreover, the intensities (areas) of the corresponding diffraction lines of the two samples were identical, suggesting that stirring or non-stirring of reactants prior to hydrothermal treatment is of little relevance regarding the subsequent product distribution after hydrothermal treatment. The results indicate that stirring is not a critical factor, so that no special precautions need to be taken in production, which is cost saving.

Examples 26-29

Effect of Water Within the Reaction Mixture (ABA140-1, 2, 3 and 4)

Four AlPO powder samples, each 2.0 g, (K00-218.002; Table 1) were mixed with 2.3 g 35% TEAOH, 0.55 g Ludox LS30 and water according to the same mixing procedure as outlined in Example 24. The difference between the reaction mixtures used in the present Examples and the corresponding reaction mixture in Example 25 was the proportion of water used (Table 2). The water content was varied with 0, 0.5, 1.0 and 3.0 in the respective mixtures. The mixtures were reacted in Teflon lined stainless steel autoclaves at 210° C. for 20 h.

Figure 9:
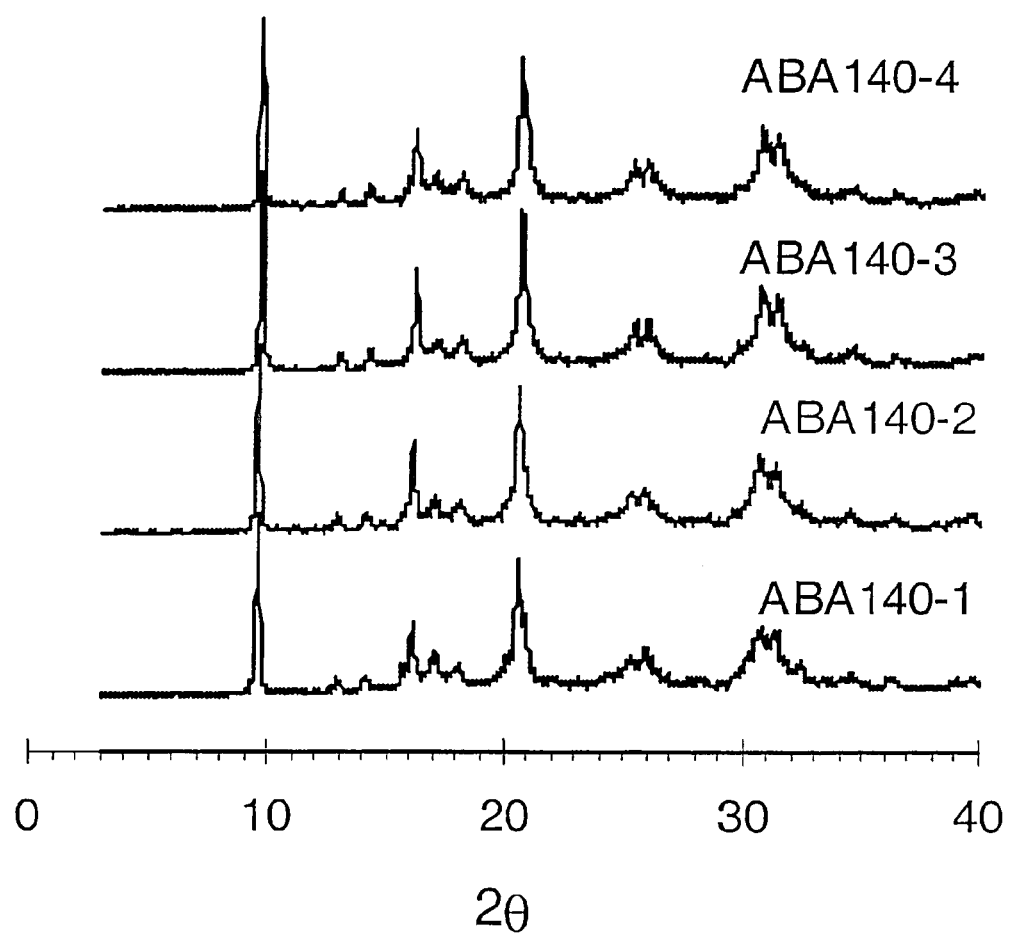
FIG. 9 shows the XRD patterns of the products from Examples 26-29.
Figure 10:
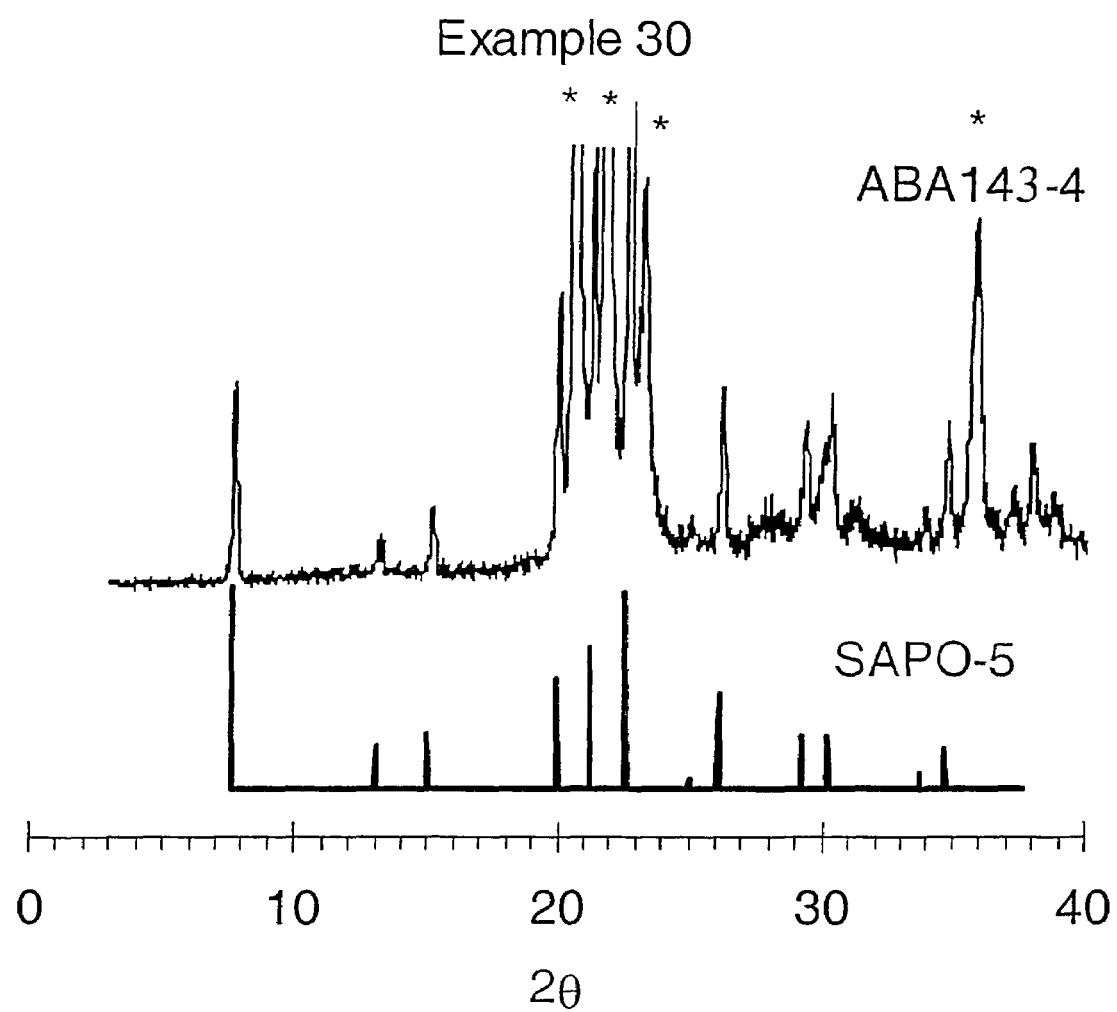
FIG. 10 shows the XRD pattern of the products from Example 30.

As was confirmed by the XRD patterns in FIG. 9, the resulting products were identical. Moreover, the intensities (areas) of the different diffraction lines of the four samples were identical, suggesting the addition of "external" water to have no significant effect on the product distribution. This result is probably not too surprising, since most of the reactants contain some "inherent" water, i.e., water contained within the actual chemical reactants used in the present synthesis (for instance 35% TEAOH and Ludox LS-30).

Example 30

Preparation of SAPO-5 (ABA143-4)

2.0 g of an AlPO "K00-058.001" powder sample (Table 1) was mixed with 0.78 g Tripropylamine, 0.55 g Ludox LS30 and 3.0 g water. The mixing and crystallisation procedures were the same as described in Example 24.

Figure 11:
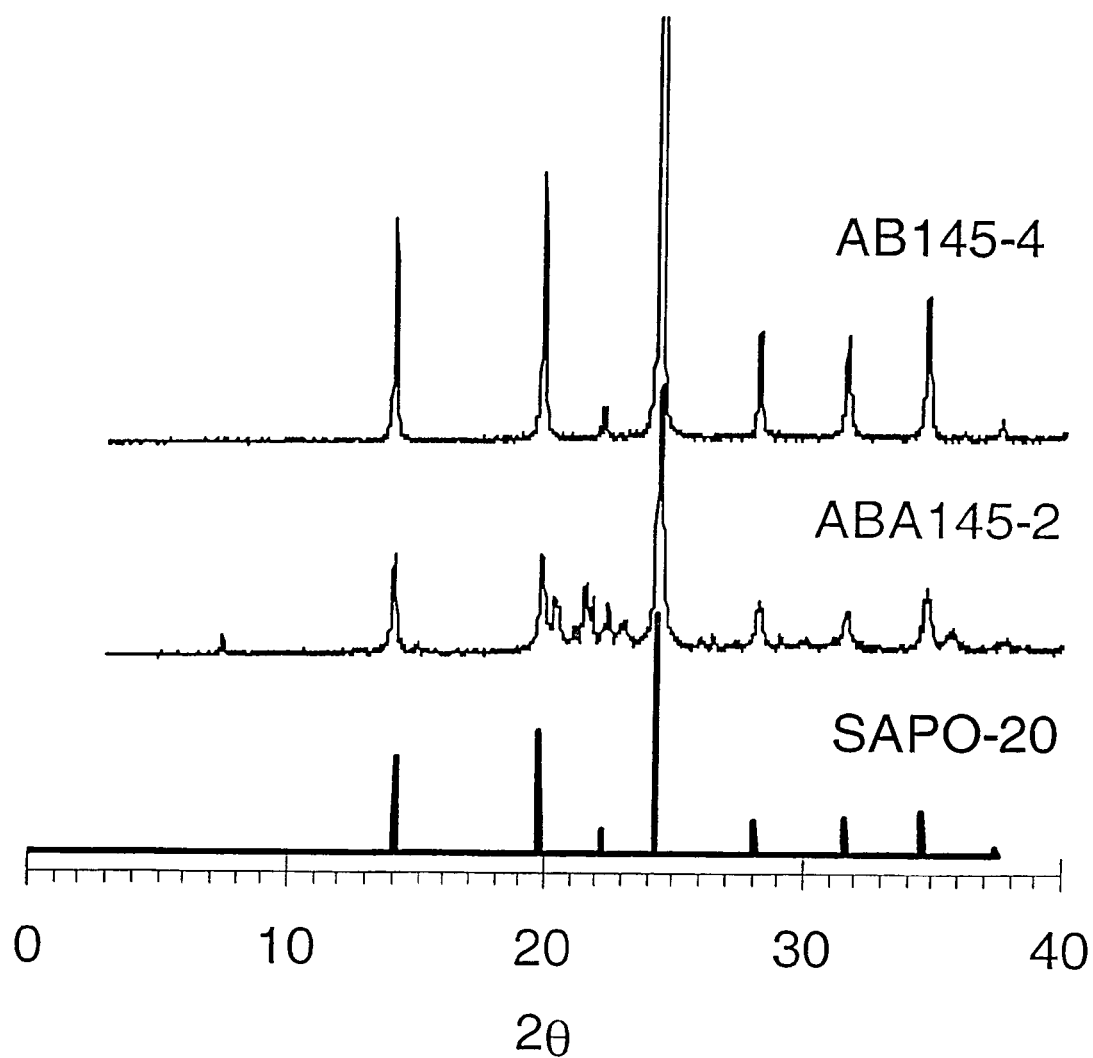
FIG. 11 shows the XRD patterns of the products from Examples 31-32.

The reference XRD pattern of SAPO-5 (FIG. 11; see "collection of simulated XRD powder patterns for zeolites", third revised edition, M. M. J. Treacy, J. B. Higgins and R. von Ballmoos, 1996) proves that a significant amount of SAPO-5 is formed from the above synthesis reaction. However, the SAPO-5 formed is not pure.

Examples 31-32

Preparation of SAPO-20 (ABA145-4, ABA-145-2)

The same type of AlPO powder as used in Example 31 ("K00-058.001"; Table 1) was mixed with Tetramethylammoniumhydroxide-pentahydrate, Ludox LS30 and water according to the same mixing and crystallisation procedure as described in Example 24. Two synthesis reactions were initiated. The amount of reactants used is shown in Table 2.

The reference XRD pattern of SAPO-20 (FIG. 11; see "collection of simulated XRD powder patterns for zeolites", third revised edition, M. M. J. Treacy, J. B. Higgins and R. von Ballmoos, 1996) shows that pure SAPO-20 may be formed from the above synthesis reaction by choosing an appropriate concentration region of chemical reactants.

Example 33

Preparation of SAPO-11 (ABA144-2)

The same type of AlPO powder (2.0 g) as used in Example 31 ("K00-058.001"; Table 1) was mixed with Diisopropylamine (0.37 g), Ludox LS30 (0.55 g) and water (3.2 g) according to the same mixing and crystallisation procedure as described in Example 24.

Figure 12:
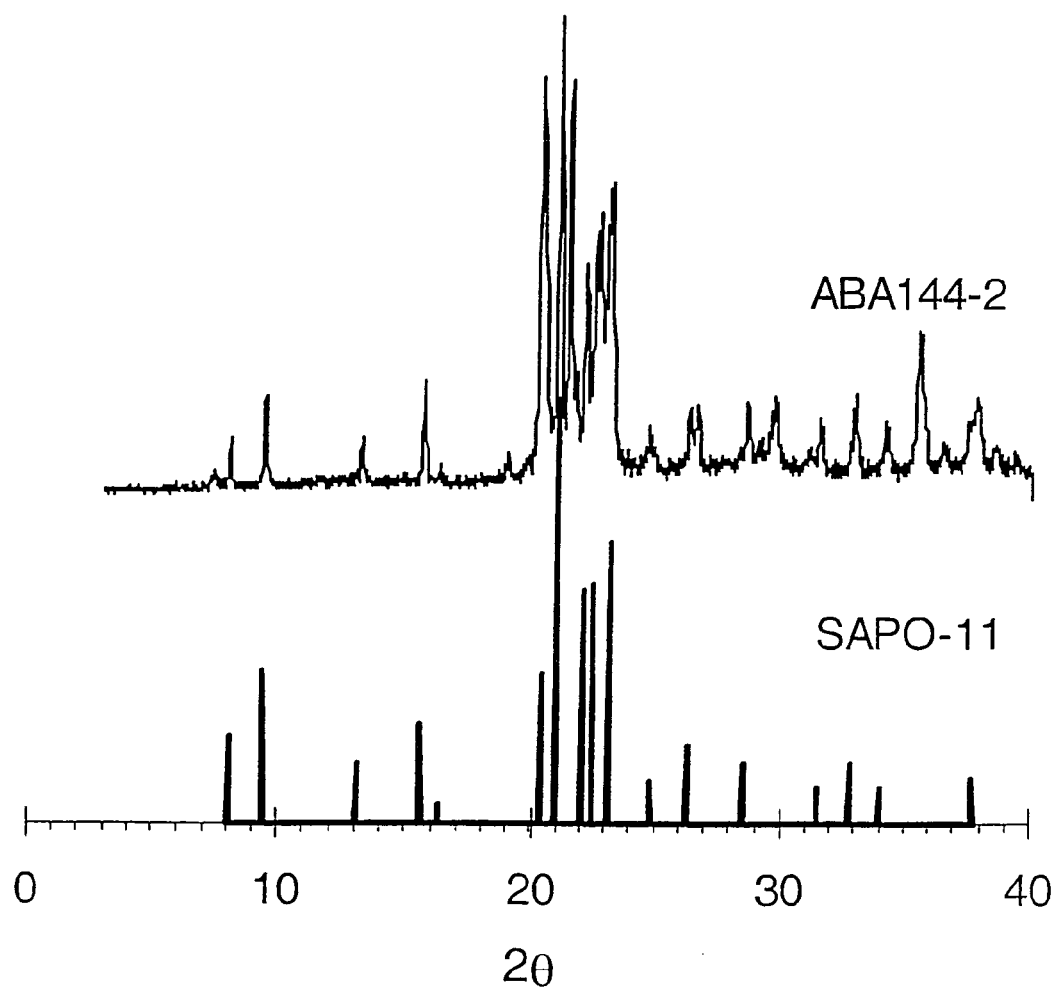
FIG. 12 shows the XRD pattern of the product from Example 33.

The reference XRD pattern of SAPO-11 in FIG. 12 (see "collection of simulated XRD powder patterns for zeolites", third revised edition, M. M. J. Treacy, J. B. Higgins and R. von Ballmoos, 1996) confirms that pure SAPO-11 may be formed from the above synthesis reaction by choosing an appropriate concentration region of the chemical reactants.

Examples 34-36

Varying the Time of Hydrothermal Treatment (ABA146-1, 2 and 3)

Figure 13:
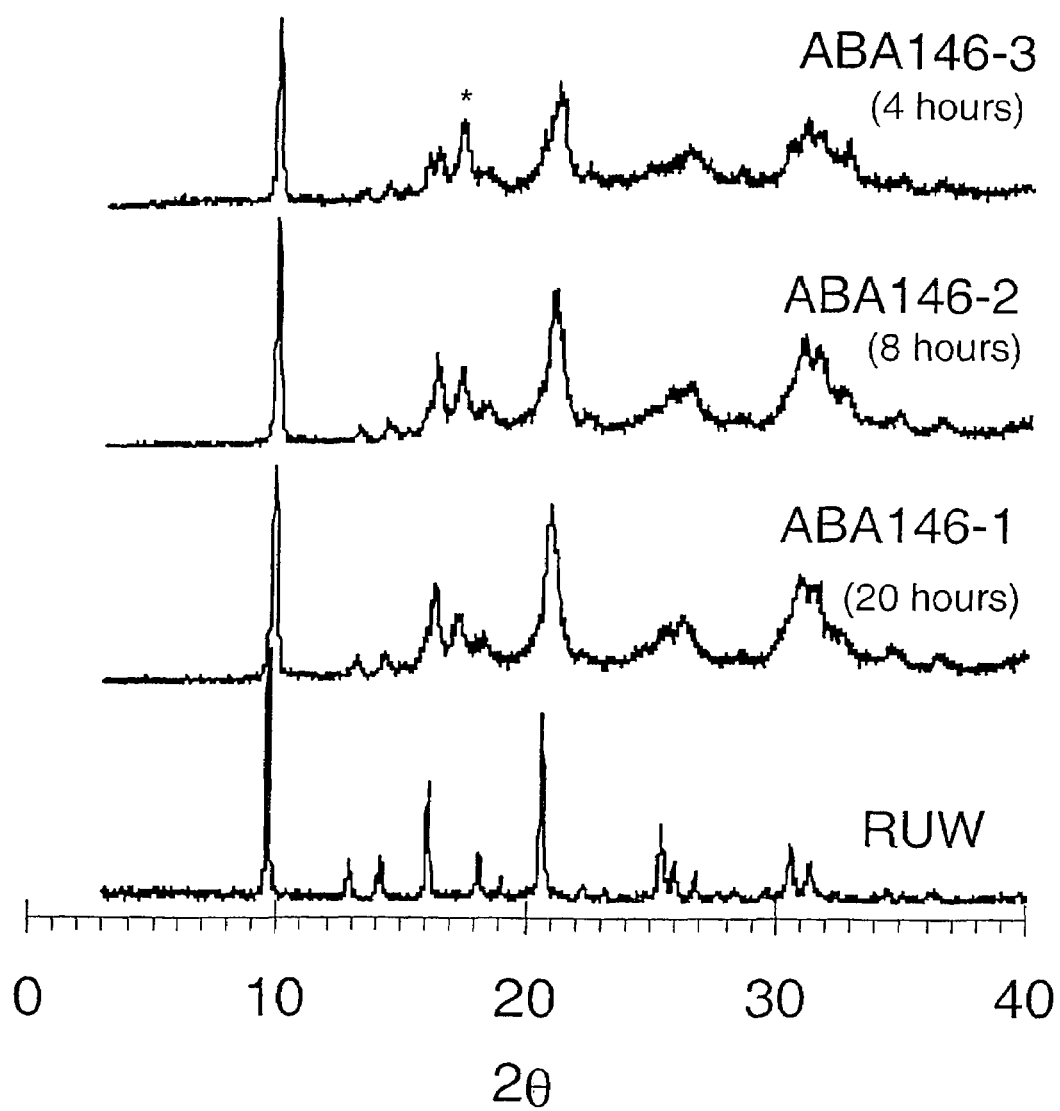
FIG. 13 shows the XRD patterns of the product from Examples 34-36.

Three products were prepared according to the synthesis recipe outlined in Example 10 and using the same porous AlPO (K00-218.002, Table 1). Only the synthesis time was varied (from 20 hours to 8 hours to 4 hours, Table 2). The XRD patterns of the respective products are illustrated in FIG. 13 and show that SAPO-34 is formed after rather short time of hydrothermal treatment, equal to or less than 4 hours. These results indicate that crystallisation time can be reduced substantially without losing product quality, which will save production costs.

Example 37-38

Synthesis of SAPO-34 with Low Amount of Structure Directing Agent (ABA147-2, ABA151-3)

Figure 14:
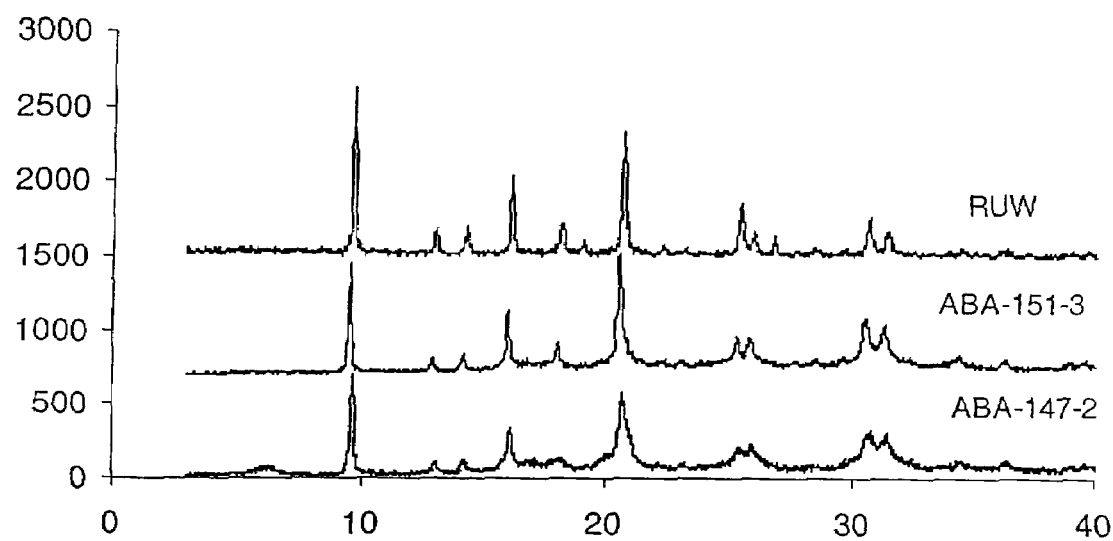
FIG. 14 shows the XRD patterns of the product from Examples 37-38

This preparation is performed according to the mixing procedure described in Examples 1-3 and using the autoclave type with Teflon insert as described in examples 4-8. Ludox LS-30 was added to AlPO (K00-058.001) and then adding TEAOH and water under thorough mixing. The synthesis temperature was 210° C. for 20 h. The XRD patterns of the respective products are illustrated in FIG. 14. From these XRD patterns we see that in spite of the low amount of structure directing agent used, SAPO-34 is obtained.

Example 39

MTO Properties in a Fixed Bed Reactor

Catalytic Testing

Catalytic tests were carried out to convert methanol into light olefins. The sample of the calcined material to be tested was compressed into tablets, which were then carefully crushed. A 35-70 mesh fraction was recovered by sieving. 1.0 g of the powder was placed in a quartz reactor and heated to 400° C. in $N_2$ and kept at this temperature for 30 min, before the temperature was increased to 420° C. and a mixture of 40% methanol and 60% nitrogen was passed through it at a WHSV=1 g MeOH/g cat/h. The product stream was analysed by gas chromatography. The catalyst lifetime was defined as the time on stream for breakthrough of dimethylether (t-DME defined as the time on stream when the Carbon selectivity to dimethylether (DME) in the effluent was=1%)

The product selectivity on a C-basis of the tested samples is set forth in Table 3. The results suggest that the SAPO-34 materials prepared from solid, porous AlPO materials by the dry syntheis method are good catalysts for the conversion of methanol into light olefins.

Table 3 contains catalytic results obtained on a limited selection of the samples shown in Table 2. The catalytic test conditions are presented in the text. A SAPO-34 sample obtained from a "traditional" wet synthesis approach (U.S. Pat. No. 4,440,871, B. M. Lok et al., Union Carbide 1984) was used as a reference sample.

TABLE 3

The catalyst lifetime given by t-DME and product selectivities at t-DME for selected samples. Reaction conditions 420° C., WHSV = 1 g/g, h and MeOH partial pressure 0.4 bar

| Product\Sample | EWH 12-4 | EWH 18-2 | EWH 16-7 | EWH 15-8 | ABA 147-2 | ABA 151-3 | Reference |
|---|---|---|---|---|---|---|---|
| Ethylene | 44.4 | 42.5 | 42.7 | 39.4 | 42.0 | 43.5 | 45.7 |
| Propene | 36.3 | 34.2 | 36.1 | 36.4 | 39.3 | 37.7 | 37.8 |
| Butenes | 11.1 | 11.6 | 11.7 | 13.5 | 12.0 | 13.2 | 9.9 |
| Methane | 2.0 | 2.0 | 1.8 | 1.8 | 2.6 | 1.5 | 1.2 |
| Ethane | 0.5 | 0.6 | 0.5 | 0.7 | 0.4 | 0.7 | 0.9 |
| Propane | 0.9 | 0.9 | 1.3 | 0 | 0 | 0 | 1.6 |
| Butanes | 0.1 | 0.2 | 0.2 | 0.3 | 0.1 | 0.3 | 0.1 |
| C5+ | 4.7 | 8.0 | 5.7 | 7.9 | 3.6 | 3.1 | 2.8 |
| t-DME; Minutes | 645 | 575 | 550 | 445 | 560 | 330 | 400 |

Example 40

MTO Properties in a Fluidized Bed Reactor

A slurry was made of the material from Example 23, the aluminium phosphate K00-218.002 (Table 1) and $SiO_2$ (Ludox HS40). The slurry was spray dried in a conventional spray drier with the outlet temperature set at approximately 100° C. The material was then calcined in an oven at 550°

C. for 8-16 h, and the final material is denoted Prototype catalyst. Elemental analysis of the material indicated 35 weight % SAPO-34.

The material was tested in a bench scale fluidised-bed reactor with on-line GC analysis. The results were compared with a generic SAPO-34 based catalyst from UOP (id 07045-16) at identical WHSV based on SAPO-34. The catalyst lifetime defined as the time on stream for breakthrough of dimethylether and the product selectivity are set forth in Table 4.

TABLE 4

Catalyst lifetime given by t-DME and product selectivities at t-DME in the MTO reaction over the Prototype catalyst and the UOP catalyst. Reaction conditions 460° C., WHSV = 1 g/g cat, h and MeOH partial pressure 0.9 bar

|  | MTO lifetime (h) | C2 = +C3 = selectivity (C %) |
|---|---|---|
| UOP catalyst | 2.3 | 85 |
| Prototype catalyst | 2.4 | 86 |

The examples show the application of the catalyst in the synthesis of light olefins from methanol.

Examples 41-44

Synthesis of SAPO-34/SAPO-18 with Si/Al Ratio<0.11 Using Different Crystallisation Temperatures Ludox LS30 was mixed together with TEAOH and the resulting solution was added to the AlPO powder (K00-218.002). The mixtures were reacted in 40 ml Teflon lined stainless steel autoclaves according to the procedure described in Examples 4-8. Temperatures and synthesis conditions are given in Table 2.

The as-synthesised catalysts were characterised by XRD to confirm formation of SAPO-34 and SAPO-18. The crystallinity as well as the relative amount of SAPO-34 and SAPO-18 was estimated by comparing the XRD diffractograms of the samples with XRD diffractograms of pure SAPO-34 and pure SAPO-18, and with theoretically calculated XRD patterns for a product with varying composition of SAPO-34/18. The micro pore volume (MPV) was measured and the catalysts were tested for the MTO reaction according to the procedure described in Example 39.

The characterisation results are given in Table 5. The results confirm that SAPO-34/18 materials are formed with Si/Al=0.06, and compared with Si/Al=0.17 (Example 41). SEM pictures of the samples confirm formation of small 0.1-0.6 µm particles. The examples show that by varying the synthesis conditions the relative contents of SAPO-34 and SAPO-18 can be controlled. The examples also show that low Si samples are very good MTO catalysts. The low initial propane selectivity and the high catalyst lifetime (t-DME) prove a low coking rate. The ethylene selectivity at t-DME is high.

Examples 45-49

Synthesis of SAPO-34/18 with Si/Al=0.06, Using Low Amounts of Structure Directing Agent Ludox LS30 was mixed together with TEAOH as well as the organic structure directing agent TEA (Example 50) and the resulting solution was added to the AlPO powder (K00-218.002). The silicon content was kept at 0.06 Si/Al, but the amount of TEAOH added in the synthesis was varied. The mixtures were reacted in 40 ml Teflon lined stainless steel autoclaves at 210° C. for 20 h according to procedure described in Example 4-8. The synthesis conditions are given in Table 2.

The samples are characterised by XRD, MPV and tested for the MTO reaction as described in Examples 41-44. The characterisation results are given in Table 5 and confirm that SAPO-34/SAPO-18 samples with Si/Al=0.06 are obtained.

The examples show that by using this synthesis procedure a good MTO catalyst can be obtained with as low as 0.33 TEAOH/Al without producing any SAPO-5 in the synthesis. Even 0.25 TEAOH/Al gives a good catalyst and the small content of SAPO-5 does not interfere with the lifetime or with the selectivity. Using 0.17 TEAOH/Al+0.17 TEA/Al also gives a good MTO catalyst.

Example 50-51

Synthesis of SAPO-34/18 with Varying Silicon Content

Ludox LS30 was mixed together with TEAOH and the resulting solution was added to the AlPO powder (K00-218.002). The amount of structure directing agent was kept constant, but the amount of Si was varied. The mixtures were reacted in 40 ml Teflon lined stainless steel autoclaves at 210° C. for 20 h according to procedure described in Examples 4-8. The synthesis conditions are given in Table 2.

The samples are characterised by XRD, MPV and tested for the MTO reaction as described in Examples 41-44. The characterisation results are given in Table 5.

The examples show that by using this synthesis procedure a good MTO catalyst is obtained with as low as 0.03 Si/Al. Example 47 shows that 0.06 Si/Al gives a good MTO catalyst with the same amount of structure directing agent as in Examples 50 and 51. The examples (46, 49 and 51) further confirm that SAPO-34/SAPO-18 is obtained. Less TEAOH and less Si tend to increase the SAPO-18 content at these crystallisation conditions.

TABLE 5

Characterisation results of catalysts in Examples 41–51

| Example | Synth. no. | Crystallinity %[2] | SAPO-34 of SAPO-18 + SAPO-34[3] (%) | t-DME (min) | Propane selectivity at TOS = 15 min. (%) | $C_2$ = selectivity at t_DME (%) | MPV (mlN$_2$/g) |
|---|---|---|---|---|---|---|---|
| 41 | ABA-201-1 | 93 | 95 | 560 | 17 | 43 | |
| 42 | ABA-201-2 | 62 | 90 | 560 | 13 | 43 | 0.20 |

TABLE 5-continued

Characterisation results of catalysts in Examples 41–51

| Example | Synth. no. | Crystallinity %[2] | SAPO-34 of SAPO-18 + SAPO-34[3] (%) | t-DME (min) | Propane selectivity at TOS = 15 min. (%) | $C_2$ = selectivity at t_DME (%) | MPV (mlN$_2$/g) |
|---|---|---|---|---|---|---|---|
| 43 | ABA-202-2 | 86 | 40 | 670 | 5 | 44 | 0.23 |
| 44 | ABA-204-2 | 91 | 90 | 660 | 8 | 46 | 0.22 |
| 45 | ABA 208-1 | 100 | 20[1] | 670 | 3 | 40 | 0.18 |
| 46 | ABA-207-2 | 92 | 20 | 625 | 2 | 40 | 0.20 |
| 47 | ABA-208-2 | 80 | 40 | | | | |
| 48 | ABA-207-1 | 77 | 50 | | | | |
| 49 | ABA-210-2 | 75 | 30[1] | 720 | 3 | 38 | |
| 50 | ABA-208-6 | 98 | 50 | | | | |
| 51 | ABA-208-5 | 81 | 15 | 645 | 2 | 41 | 0.23 |

[1] Small amounts of SAPO-5 is formed
[2] The crystallinity is obtained from the integral of the 2θ = 9.6, assuming SAPO-34 and SAPO-18 behaves similarly and ABA-208-1 is set to 100%
[3] The relative amount of SAPO-34 and SAPO-18 was determined by comparing the XRD diffractograms of the samples with XRD diffractograms of pure SAPO-34 and pure SAPO-18

The invention claimed is:

1. Method of synthesising crystalline microporous metalloaluminophosphate (ELAPO) from a solid body, where the body consists of particles containing mainly aluminiumphosphates (AlPO$_4$) and where the particles have pores wholly or partly filled with a liquid reaction mixture, comprising an active source of the EL metal, an organic structure directing agent and water, the method comprising performing crystallisation at elevated temperature under autogenous pressure to form crystals of microporous ELAPO, where the EL metal is selected from the group consisting of silicon, magnesium, zinc, iron, cobolt, nickel, manganese, chromium and mixtures thereof.

2. A method according to claim 1, wherein the method is conducted at a H$_2$O/Al ratio of 5-10.

3. Method according to claim 1, wherein the EL metal is silicon and where crystalline microporous SAPO is produced.

4. Method according to claim 3, wherein the ELAPO is SAPO-34, SAPO-17, SAPO-18 or mixtures thereof.

5. Method according to claim 3, wherein the ELAPO is SAPO-5, SAPO-11 or SAPO-20.

6. Method according to claim 3, wherein the organic structure directing agent is one or more members selected from the group consisting of tetraethyl ammonium hydroxide (TEAOH), isopropylamine (IPA), diisopropylamine (DPA), tripropylamine (TPA), cyclohexylamine (CHA), triethylamine (TEA) and tetramethyl-ammonium-hydroxide (TMAOH).

7. A method according to claim 1, wherein the AlPO$_4$ used has P/Al=1.2-0.6.

8. Method according to claim 1, wherein the particles are AlPO$_4$ particles with an outer silica shell.

9. Method according to claim 1, wherein the synthesising is carried out in the absence of an external liquid.

10. Method according to claim 1, wherein the crystallisation is performed at temperatures from 150-260° C.

11. A method according to claim 10, wherein the temperature is 200-220° C.

12. Method according to claim 1, wherein the hydrothermal reaction time is 2-120 hours.

13. A method according to claim 12, wherein the reaction time is 4-20 hours.

14. Method according to claim 1 wherein the particles are calcined prior to the crystallisation.

15. Method according to claim 1, wherein the ratio between the liquid volume and pore volume is 0.1-7.

16. A method according to claim 15, wherein the ratio is 1-4.

17. A method according to claim 15, wherein the ratio is 1-3.

18. Method according to claim 1, wherein the ELAPO is SAPO-34, SAPO-17, SAPO-18 or mixtures thereof.

19. Method according to claim 1, wherein the ELAPO is SAPO-5, SAPO-11 or SAPO-20.

20. Method according to claim 1, wherein the organic structure directing agent is one or more members selected from the group consisting of tetraethyl ammonium hydroxide (TEAOH), isopropylamine (IPA), diisopropylamine (DPA), tripropylamine (TPA), cyclohexylamine (CHA), triethylamine (TEA) and tetramethyl-ammonium-hydroxide (TMAOH).

21. Method according to claim 1, wherein the El/Al ratio is in the range 0.01-0.5.

22. A method according to claim 21, wherein the El/Al ratio is 0.03-0.17.

23. Method according to claim 1, wherein the Si/Al ratio is in the range 0.01-0.5.

24. A method according to claim 23, wherein the Si/Al ratio is 0.03-0.17.

25. Method according to claim 1, wherein ELAPO is produced from a reaction mixture without stirring of the reactants.

26. A method for the production of olefins from an oxygenate containing feedstock comprising at least one compound selected from the group consisting of methanol, ethanol, n-propanol, iso-propanol, C4-C20 alcohols, methyl ethyl ether, dimethyl ether, diethyl ether, di-isopropyl ether, formaldehyde, dimethyl carbonate, dimethyl ketone, acetic acid and mixtures thereof, which comprises heating the feedstock in the presence of the crystalline microporous metalloaluminophosphate produced according claim 1.

27. Method of synthesising crystalline microporous metalloaluminophosphate (ELAPO) from a solid body, wherein the body consists of particles containing mainly EL metal and aluminiumphosphates (AlPO$_4$) where the particles have pores wholly or partly filled with a liquid reaction mixture comprising an organic structure directing agent and water, and the method comprising performing crystallisation at elevated temperature under autogenous pressure to form crystals of microporous ELAPO where the EL metal is selected from the group consisting of silicon, magnesium, zinc, iron, cobolt, nickel, manganese, chromium and mixtures thereof.

28. A method according to claim 27, wherein the method is conducted at a $H_2O$/Al ratio of 5-10.

29. A method according to claim 27, wherein the liquid reaction mixture also contains an active source of a metal EL.

30. A method according to claim 29, where the metal is silicon.

31. Method according to claim 27, wherein the EL metal is silicon and where crystalline microporous SAPO is produced.

32. Method according to claim 31, wherein the ELAPO is SAPO-34, SAPO-17, SAPO-18 or mixtures thereof.

33. Method according to claim 31, wherein the ELAPO is SAPO-5, SAPO-11 or SAPO-20.

34. Method according to claim 31, wherein the organic structure directing agent is one or more members selected from the group consisting of tetraethyl ammonium hydroxide (TEAOH), isopropylamine (IPA), diisopropylamine (DPA), tripropylamine (TPA), cyclohexylamine (CHA), triethylamine (TEA) and tetramethyl-ammonium-hydroxide (TMAOH).

35. A method according to claim 27, wherein the $AlPO_4$ used has P/Al=1.2-0.6.

36. A method according to claim 27, wherein the particles are $AlPO_4$ particles with an outer silica shell.

37. A method according to claim 27, wherein the synthesising is carried out in the absence of an external liquid.

38. Method according to claim 27, wherein the crystallisation is performed at temperatures from 150-260° C.

39. A method according to claim 38, wherein the temperature is 200-220° C.

40. Method according to claim 27, wherein the hydrothermal reaction time is 2-120 hours.

41. A method according to claim 40, wherein the reaction time is 4-20 hours.

42. Method according to claim 27, wherein the particles are calcined prior to the crystallisation.

43. Method according to claim 27, wherein the ratio between the liquid volume and pore volume is 0.1-7.

44. A method according to claim 43, wherein the ratio is 1-4.

45. A method according to claim 43, wherein the ratio is 1-3.

46. Method according to claim 27, wherein the ELAPO is SAPO-34, SAPO-17, SAPO-18 or mixtures thereof.

47. Method according to claim 27, wherein the ELAPO is SAPO-5, SAPO-11 or SAPO-20.

48. Method according to claim 27, wherein the organic structure directing agent is one or more members selected from the group consisting of tetraethyl ammonium hydroxide (TEAOH), isopropylamine (IPA), diisopropylamine (DPA), tripropylamine (TPA), cyclohexylamine (CHA), triethylamine (TEA) and tetramethyl-ammonium-hydroxide (TMAOH).

49. Method according to claim 27, wherein ELAPO is produced from a reaction mixture without stirring of the reactants.

50. A method for the production of olefins from an oxygenate containing feedstock comprising at least one compound selected from the group consisting of methanol, ethanol, n-propanol, iso-propanol, C4-C20 alcohols, methyl ethyl ether, dimethyl ether, diethyl ether, di-isopropyl ether, formaldehyde, dimethyl carbonate, dimethyl ketone, acetic acid and mixtures thereof, which comprises heating the feedstock in the presence of the crystalline microporous metalloaluminophosphate produced according claim 27.

* * * * *